US011953493B2

(12) United States Patent
Loupis et al.

(10) Patent No.: US 11,953,493 B2
(45) Date of Patent: Apr. 9, 2024

(54) BIOPHOTONIC METHODS FOR INCREASING IN SITU ENERGY PRODUCTION AND ENERGY EMISSION IN BIOLOGICAL CELLS AND TISSUES

(71) Applicant: FLE INTERNATIONAL S.R.L., San Benedetto del Tronto (IT)

(72) Inventors: Nikolaos Loupis, Athens (GR); Remigio Piergallini, San Benedetto del Tronto (IT); David Ohayon, Dollard des Ormeaux (CA); Lise Hébert, Montreal (CA); Giovanni Scapagnini, Catania (IT)

(73) Assignee: FLE INTERNATIONAL S.R.L., San Benedetto del Tronto (IT)

( * ) Notice: Subject to any disclaimer, the term of this patent is extended or adjusted under 35 U.S.C. 154(b) by 1191 days.

(21) Appl. No.: 16/483,479

(22) PCT Filed: Feb. 8, 2018

(86) PCT No.: PCT/CA2018/050146
§ 371 (c)(1),
(2) Date: Aug. 5, 2019

(87) PCT Pub. No.: WO2018/145208
PCT Pub. Date: Aug. 16, 2018

(65) Prior Publication Data
US 2019/0360993 A1 Nov. 28, 2019

Related U.S. Application Data

(60) Provisional application No. 62/456,246, filed on Feb. 8, 2017.

(51) Int. Cl.
*G01N 33/48* (2006.01)
*A61B 5/00* (2006.01)
(Continued)

(52) U.S. Cl.
CPC .......... *G01N 33/48* (2013.01); *A61B 5/0071* (2013.01); *A61K 31/352* (2013.01);
(Continued)

(58) Field of Classification Search
CPC ...................................... A61N 5/062
See application file for complete search history.

(56) References Cited

U.S. PATENT DOCUMENTS 6,086,580 A * 7/2000 Mordon ................ A61N 5/062
606/9

FOREIGN PATENT DOCUMENTS

| CA | 2742942 A1 | 5/2010 |
| CA | 2742943 A1 | 5/2010 |
| CA | 2767889 A1 | 1/2011 |

OTHER PUBLICATIONS

Brock et al., "Use of In Vitro and In Vivo Data in the Design, Development, and Quality Control of Sustained-Release Decongestant Dosage Forms", Pharmacotherapy, vol. 14, No. 4, 1994.
(Continued)

*Primary Examiner* — Rosanne Kosson
(74) *Attorney, Agent, or Firm* — BCF LLP

(57) ABSTRACT

The present technology generally relates to a method for modulating in situ production of energy by a biological tissue. The method comprises stimulating the biological tissue by exposing the biological tissue to a photostimulated biophotonic composition for a time sufficient to initiate the production of energy by the biological tissue.

19 Claims, 30 Drawing Sheets

(51) Int. Cl.
*A61K 31/352* (2006.01)
*A61K 41/00* (2020.01)
*A61N 5/06* (2006.01)
*A61P 17/02* (2006.01)

(52) U.S. Cl.
CPC .......... *A61K 41/0057* (2013.01); *A61N 5/062* (2013.01); *A61P 17/02* (2018.01)

(56) References Cited

OTHER PUBLICATIONS

Cervinkova et al., "Chemical modulation of the ultra-weak photon emission from *Saccharomyces cerevisiae* and differentiated HL-60 cells", Proceedings of SPIE, 2015, 9450.

Chang, "Physical properties of biophotons and their biological functions", Indian Journal of Experimental Biology, 2008, 46, 371-377.

Cheun et al., "Biophoton emission of MDCK cell with hydrogen peroxide and 60 Hz AC magnetic field", Journal of Environmental Biology, 2007, 28(4), 735-740.

Cifra et al., "Ultra-weak photon emission from biological samples: Definition, mechanims, properties, detection and applications", Journal of Photochemistry and Photobiology B: Biology, 2014, 139, 2-10.

Durrani et al., "Studies on Drugs Release Kinetics From Carbopol® 934P Tablets", Pharmaceutical Res. Supp. 8: S-135, 1991—abstract only.

Hossu et al., "Enhancement of biophoton emission of prostate cancer cells by Ag nanoparticles", Cancer Nano, 2013, 4, 21-26.

Kim et al., "Biophoton emission induced by ultrasonic irradiation", IFMBE Proceedings, 2007, 14(1), 1277-1280.

Pospisil et al., "Role of reactive oxygen species in ultra-weak photon emission in biological systems", Journal of Photochemistry and Photobiology B: Biology, 2014, 139, 11-23.

Raffi-Tabar et al., "Different aspects of ultra-weak photon emission: A review article", Iranian Journal of Medical Physics, 2015, 12(3), 137-144.

Sharman et al., "Role of activated oxygen species in photodynamic therapy", Methods in Enzymology, 2000, 319, 376-400.

Yang, "The application of ultra-weak photon emission in dermatology", Journal of Photochemistry and Photobiology B: Biology, 2014, 139, 63-70.

* cited by examiner

* Indicate a local wound made accidently with a nail trimmer

BIOPHOTONIC METHODS FOR INCREASING IN SITU ENERGY PRODUCTION AND ENERGY EMISSION IN BIOLOGICAL CELLS AND TISSUES

CROSS-REFERENCE TO RELATED APPLICATION

The present application claims the benefit of and priority to U.S. provisional patent application No. 62/456,246, filed Feb. 8, 2017, the content of which is herein incorporated in tis entirety by reference.

FIELD OF TECHNOLOGY

The present technology relates to methods and systems for modulating the production of energy by biological tissues. The present technology also relates to methods and systems for modulating emission of energy by biological tissues.

BACKGROUND INFORMATION

Organisms are known to emit spontaneous ultra-weak photons which are differentiated from the phenomenon of delayed luminescence as it is spontaneously emitted by living organisms without any photoexcitation. The intensity of ultra-weak photon emission is found to be in the order of $10^{-16}$-$10^{-18}$ W/cm$^2$ which is far behind the sensitivity of the human eye.

Current development in detection using low-noise photomultiplier tubes (PMT) and imaging using highly sensitive charge coupled device (CCD) cameras allows temporal and spatial visualization of oxidative metabolic or oxidative stress processes, respectively. As the phenomenon of ultra-weak photon emission reflects metabolic processes, PMT and CCD can be used as a non-invasive tool for monitoring the physiological energy state of biological systems.

Although emission of spontaneous ultra-weak photons by living organisms has been observed, there is to date, no methods of modulating the production and emission of ultra-weak photons by living organisms, and as such there remains a need in the art for development of such methods.

BRIEF DESCRIPTION OF DRAWINGS

Further features and advantages of the present disclosure will become apparent from the following detailed description, taken in combination with the appended drawings, in which.

DESCRIPTION OF TECHNOLOGY

Figure 1:
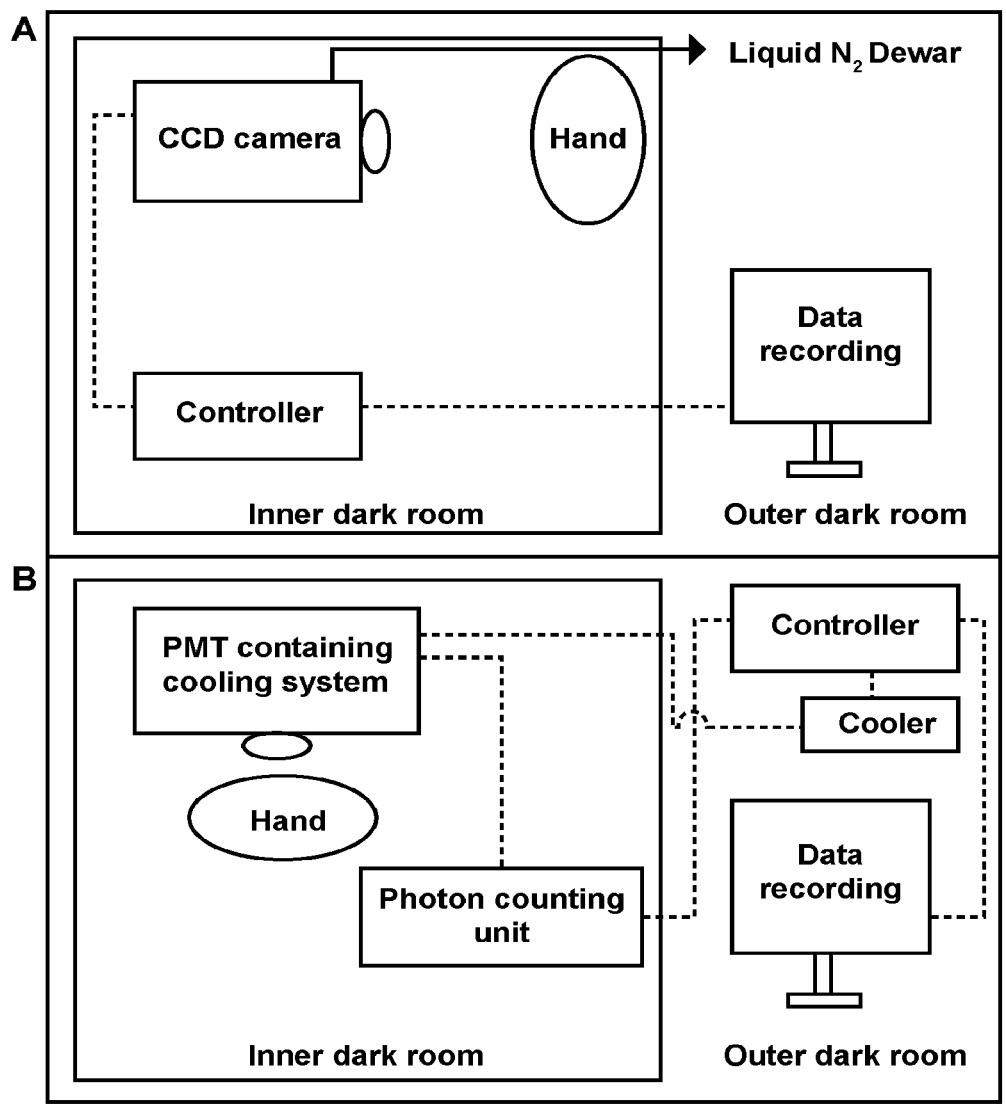
FIGS. 1A-1B are schematic representations of an experimental setup according to one embodiment of the present disclosure, wherein FIG. 1A (top panel) shows a CCD camera setup and FIG. 1B (bottom panel) shows a PMT system setup.

The present technology is explained in greater detail below. This description is not intended to be a detailed catalog of all the different ways in which the technology may be implemented, or all the features that may be added to the instant technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant technology. Hence, the following specification is intended to illustrate some particular embodiments of the technology, and not to exhaustively specify all permutations, combinations and variations thereof.

As used herein, the singular form "a," "an" and "the" include plural referents unless the context clearly dictates otherwise.

The term "about" is used herein explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

The expression "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As used herein, the term "biophotonic" means the generation, manipulation, detection and application of photons in a biologically relevant context. In other words, biophotonic compositions exert their physiological effects primarily due to the generation and manipulation of photons. As used herein, the expression "biophotonic composition" refers to a composition as described herein that may be activated by light to produce photons for biologically relevant applications.

The term "topical" as used herein means as applied to body surfaces, such as the skin, mucous membranes, vagina, oral cavity, internal surgical wound sites, and the like.

Terms and expressions "light-absorbing molecule", "chromophore", "fluorophore", "photostimulating agent," and "photostimulator" are used herein interchangeably. A light-accepting molecule means a compound, when contacted by light irradiation, is capable of absorbing the light. The light-accepting molecule readily undergoes photoexcitation and can then transfer its energy to other molecules or emit it as light.

The present technology stems from studies by the discoverers which aimed at determining the effects of fluorescence emitted by the biophotonic compositions of the present disclosure on the ability of biological tissues to produce and emit energy.

The discoverers have surprisingly found that stimulation of biological tissues by the fluorescence emitted from the biophotonic compositions as defined herein causes an increase in in-situ production and emission of energy by the biological tissue. In addition, the discoverers have observed that such in-situ production and emission of energy by the biological tissues is maintained once the stimulation is stopped.

According to one embodiment, the present disclosure thus provides a method for modulating in situ production of energy by a biological tissue. In some aspects, the method comprises stimulating the biological tissue by exposing the biological tissue to a photostimulated biophotonic composition as defined herein, for a time sufficient for the fluorescence to initiate production of energy by the biological tissue. In some aspects, the method comprises stimulating the biological tissue by exposing the biological tissue to fluorescence emitted by a photostimulated biophotonic composition as defined herein, for a time sufficient for the fluorescence to initiate production of energy by the biological tissue.

According to another embodiment, the present disclosure provides a method for modulating in situ emission of energy by a biological tissue. In some aspects, the method comprises stimulating the biological tissue by exposing the biological tissue to a photostimulated biophotonic composition as defined herein, for a time sufficient for the fluorescence to initiate emission of energy by the biological tissue. In some aspects, the method comprises stimulating the biological tissue by exposing the biological tissue to fluorescence emitted by a photostimulated biophotonic composition as defined herein, for a time sufficient for the fluorescence to initiate emission of energy by the biological tissue.

In some aspects of these embodiments, modulation of the in situ energy production and emission by a biological tissue is achieved by varying the duration of stimulation of the biological tissue. Such may be achieved by varying the period of time during which a biological tissue is exposed to fluorescence emitted by the biophotonic composition.

In some aspects of these embodiments, modulation of the in situ energy production and emission by a biological tissue is achieved by varying the properties of the fluorescence emitted by the biophotonic composition. Such may be achieved by using light-accepting molecules with different spectral emission properties and/or by using combinations of light-accepting molecules having different spectral emission properties.

According to another embodiment, the present disclosure thus provides a method for increasing in situ production of energy of a biological tissue. In some aspects, the method comprises stimulating the biological tissue by exposing the biological tissue to a photostimulated biophotonic composition as defined herein, for a time sufficient for the fluorescence to increase production of energy by the biological tissue. In some aspects, the method comprises stimulating the biological tissue by exposing the biological tissue to fluorescence emitted by a photostimulated biophotonic composition as defined herein, for a time sufficient for the fluorescence to increase production of energy by the biological tissue.

According to another embodiment, the present disclosure provides a method for increasing in situ emission of energy by a biological tissue. In some aspects, the method comprises stimulating the biological tissue by exposing the biological tissue to a photostimulated biophotonic composition as defined herein, for a time sufficient for the fluorescence to increase emission of energy by the biological tissue. In some aspects, the method comprises stimulating the biological tissue by exposing the biological tissue to fluorescence emitted by a photostimulated biophotonic composition as defined herein, for a time sufficient for the fluorescence to increase emission of energy by the biological tissue.

In some aspects of these embodiments, the fluorescence emitted by the biophotonic composition may be used to modify the emission pattern of the biological tissue.

According to another embodiment, the present disclosure thus provides a method for enhancing metabolic activities of a biological tissue. In some aspects, the method comprises stimulating the biological tissue by exposing the biological tissue to a photostimulated biophotonic composition as defined herein, for a time sufficient for the fluorescence to enhance metabolic activities of the biological tissue. In some aspects, the method comprises stimulating the biological tissue by exposing the biological tissue to fluorescence emitted by a photostimulated biophotonic composition as defined herein, for a time sufficient for the fluorescence to enhancing metabolic activities of the biological tissue.

As used herein, the expression "in-situ production" or "in-situ emission" of energy by the biological tissue indicates that the production of energy occurs within the biological tissue itself or that the energy is emitted by the biological tissue itself.

In some aspects of these embodiments, the energy is ultra-weak photon emission. As used herein, the expression "ultra-weak photon emission" refers to the chemiluminescence originating from biological tissues which is the result of biochemical reactions in which electrons transition in and out of electronically excited states.

In some embodiment, the efficiency of a biophotonic composition at modulating in situ energy production and/or in situ energy emission by a biological tissue is indicated by the photon emission index (PE index) of the biophotonic composition for that particular biological tissue. As used herein, the PE index of a biophotonic composition corresponds to the amount of time it takes for the biological tissue photostimulated by the biophotonic composition, to reach a photon emission that is about 10% of its initial photon emission (following photostimulation). A long PE index suggests that the biological tissue photostimulated by the specific biophotonic composition emits photons over a prolonged period of time whereas a short PE index suggests that the biological tissue photostimulated by that specific biophotonic composition emits photons over a short period of time.

In some implementations, the PE index may be modulated by varying the composition of the biophotonic compositions used to photostimulate the biological tissue, such as, for example, by varying the type of light-absorbing molecule present in the composition and/or varying its concentration. In some implementations of this embodiments, the PE index of the biological compositions of the present disclosure is at least about 30 seconds, at least about 1 minute, at least about 2 minutes, at least about 3 minutes, at least about 4 minutes, at least about 5 minutes, at least about 6 minutes, at least about 7 minutes, at least about 8 minutes, at least about 9 minutes, or at least about 10 minutes. In some other embodiments, the PE index of the biological compositions of the present disclosure is between about 30 seconds and about 15 minutes, or between about 30 seconds and about 10 minutes, or between about 30 seconds and about 5 minutes.

In some aspects of these embodiments, the expression "biological tissue" refers to any organ and tissue of a living system or organism. Examples of biological tissue include, but are not limited to: brain, the cerebellum, the spinal cord, the nerves, blood, lungs, heart, blood vessels, skin, hair, fat, nails, bones, cartilage, ligaments, tendons, ovaries, fallopian tubes, uterus, vagina, mammary glands, testes, vas deferens, seminal vesicles, prostate, salivary glands, esophagus, stomach, liver, gallbladder, pancreas, intestines, rectum, anus, kidneys, ureters, bladder, urethra, the pharynx, larynx, bronchi, lungs, diaphragm, hypothalamus, pituitary gland, pineal body or pineal gland, thyroid, parathyroid, adrenals (e.g., adrenal glands), lymph nodes and vessels, skeletal muscles, smooth muscles, cardiac muscle, brain, spinal cord, peripheral nervous system, ears, eyes, nose, and the like.

In other aspects of these embodiments, the expression "biological tissue" refers to individual cells or a population or a group of cells. In some instances, the cells are ex vivo cells. In some other instances, the cells are in vivo. In some other instances, the cells are in vitro.

As used herein, the expression "metabolic activities" or "metabolism" refers to life-sustaining chemical transformations within the cells of living organisms. The word metabolism can also refer to the sum of all chemical reactions that occur in living organisms, including digestion and the transport of substances into and between different. Metabolism is usually divided into two categories: catabolism, the breaking down of organic matter, for example, by cellular respiration, and anabolism, the building up of components of cells such as proteins and nucleic acids. The chemical reactions of metabolism are organized into metabolic pathways, in which one chemical is transformed through a series of steps into another chemical, by a sequence of enzymes. Enzymes are crucial to metabolism because they allow organisms to drive desirable reactions that require energy that will not occur by themselves, by coupling them to spontaneous reactions that release energy. Enzymes act as catalysts that allow the reactions to proceed more rapidly. Enzymes also allow the regulation of metabolic pathways in response to changes in the cell's environment or to signals from other cells.

Biophotonic compositions according to the present disclosure are compositions that are, in a broad sense, activated by light (e.g., photons) of a specific wavelength. These compositions comprise at least one exogenous light-accepting molecule (e.g., a light-accepting molecule that is not naturally present in skin or tissue of the patient being treated), which is activated by light and accelerates the dispersion of light energy, which leads to light carrying on a therapeutic effect on its own, and/or to the photochemical activation of other agents comprised in the composition. The composition may comprise an agent which, when mixed with a light-accepting molecule or combination of light-accepting molecules and subsequently activated by light, can be photochemically activated.

When a light-accepting molecule absorbs a photon of a certain wavelength, it becomes excited. This is an unstable condition and the molecule tries to return to the ground state, giving away the excess energy. For some light-accepting molecules, it is favorable to emit the excess energy as light when transforming back to the ground state. This process is called fluorescence. The peak wavelength of the emitted fluorescence is shifted towards longer wavelengths compared to the absorption wavelengths ('Stokes' shift'). The emitted fluorescent energy can then be transferred to the other components of the composition or to a tissue on to which the biophotonic composition is applied.

Differing wavelengths of light may have different and complementary effects on the biological tissue.

Without being bound to theory, it is thought that fluorescent light emitted by photostimulated light-accepting molecules may have therapeutic properties due to its femto-, pico- or nano-second emission properties which may be recognized by biological cells and tissues, leading to favorable biomodulation. Furthermore, the emitted fluorescent light has a longer wavelength and hence a deeper penetration into the tissue than the activating light.

In certain embodiments, the biophotonic compositions of the present disclosure are substantially transparent/translucent and/or have high light transmittance in order to permit light dissipation into and through the composition. The % transmittance of the biophotonic composition can be measured in the range of wavelengths from 250 nm to 800 nm using, for example, a Perkin-Elmer Lambda™ 9500 series UV-visible spectrophotometer. Alternatively, a Synergy™ HT spectrophotometer (BioTek Instrument, Inc.) can be used in the range of wavelengths from 380 nm to 900 nm.

The biophotonic composition can be in the form of a semi-solid or viscous liquid, such as a gel, or are gel-like, and which have a spreadable consistency at room temperature (e.g., about 20-25° C.), prior to illumination. By spreadable is meant that the composition can be topically applied to a tissue at a thickness of less than about 0.5 mm, from about 0.5 mm to about 3 mm, from about 0.5 mm to about 2.5 mm, or from about 1 mm to about 2 mm Spreadable compositions can conform to a topography of a site onto which it is to be applied. This can have advantages over a non-conforming material in that a better and/or more complete illumination of the site can be achieved and the compositions are easy to apply and remove.

The biophotonic compositions may be described based on the components making up the composition. Additionally or alternatively, the compositions of the present disclosure have functional and structural properties and these properties may also be used to define and describe the compositions. Individual components of the composition of the present disclosure are detailed below.

In some embodiments, the biophotonic compositions of the present disclosure comprise an oxidant selected from, but not limited to, hydrogen peroxide, urea hydrogen peroxide, benzoyl peroxide, peroxy acids, or alkali metal percarbonates.

Suitable oxidants for the biophotonic compositions of the present disclosure include, but are not limited to: hydrogen peroxide ($H_2O_2$). Hydrogen peroxide for use in this composition can be used in a gel, for example with 6% hydrogen peroxide by weight of the total composition. A suitable range of concentration over which hydrogen peroxide can be used in a composition of the present disclosure is less than about 12% by weight of the total compositions. In some embodiments, hydrogen peroxide is present in an amount from about 0.1% to about 12%, from about 1% to about 12%, from about 3.5% to about 12%, from about 3.5% to about 6%, or from about 0.1% to about 6% by weight of the total composition.

Urea hydrogen peroxide (also known as urea peroxide, carbamide peroxide or percarbamide) is soluble in water and contains about 36% hydrogen peroxide. Carbamide peroxide for use in this composition can be used as a gel, for example with about 16% carbamide peroxide that represents about 5.6% hydrogen peroxide. A suitable range of concentration over which urea peroxide can be used in a composition of the present disclosure is less than about 36% by weight of the total composition. In some embodiments, urea peroxide is present in an amount from about 0.3% to about 36%, such as from about 3% to about 36%, from about 10% to about 36%, from about 3% to about 16%, from about 3% to about 9%, or from about 0.3% to about 16% by weight of the total composition. In some embodiments, urea peroxide is present in an amount of about 2% by weight of the total composition. In some embodiments, urea peroxide is present in an amount of about 3% by weight of the total composition. In some embodiments, urea peroxide is present in an amount of about 6% by weight of the total composition. In some embodiments, urea peroxide is present in an amount of about 8% by weight of the total composition. In some embodiments, urea peroxide is present in an amount of about 9% of the total composition. In some embodiments, urea peroxide is present in an amount of about 12% by weight of the total composition.

Benzoyl peroxide consists of two benzoyl groups (benzoic acid with the H of the carboxylic acid removed) joined by a peroxide group. The released peroxide groups are effective at killing bacteria. Benzoyl peroxide also promotes skin turnover and clearing of pores. Benzoyl peroxide breaks down to benzoic acid and oxygen upon contact with skin, neither of which is toxic. A suitable range of concentration over which benzoyl peroxide can be used in the present composition is less than about 10% by weight of the total composition, such as from about 1% to 10%, from about 1% to 8%, from about 2.5% to about 5%. In some embodiments, benzoyl peroxide is present in an amount from about 1% to about 10%, or from about 1% to about 8%, or from about 2.5% to about 5% by weight of the total composition.

In some embodiments, the biophotonic topical compositions of the present disclosure comprise one or more light-accepting molecules, which can be considered exogenous, e.g., are not naturally present in skin or tissue. When a biophotonic composition of the present disclosure is illuminated with light, the light-accepting molecule(s) are excited to a higher energy state. When the light-accepting molecule(s)' electrons return to a lower energy state, they emit photons with a lower energy level, thus causing the emission of light of a longer wavelength (Stokes' shift).

Suitable light-accepting molecules for the biophotonic compositions of the disclosure can be fluorescent dyes (or stains), although other dye groups or dyes (biological and histological dyes, food colorings, carotenoids, naturally occurring fluorescent and other dyes) can also be used.

In some embodiments, the biophotonic topical composition of the present disclosure comprises a light-accepting molecule which undergoes partial or complete photobleaching upon application of light. By photobleaching is meant a photochemical destruction of the light-accepting molecule which can generally be characterized as a visual loss of color or loss of fluorescence.

In some embodiments, the light-accepting molecule absorbs at a wavelength in the range of the visible spectrum, such as at a wavelength of from about 380 to about 800 nm, such as from about 380 to about 700 nm, or from about 380 to about 600 nm. In some embodiments, the light-accepting molecule absorbs at a wavelength of from about 200 to about 800 nm, such as from about 200 to about 700 nm, from about 200 to about 600 nm, or from about 200 to about 500 nm. In some embodiments, the light-accepting molecule absorbs at a wavelength of from about 200 to about 600 nm. In some embodiments, the light-accepting molecule absorbs light at a wavelength of from about 200 to about 300 nm, from about 250 to about 350 nm, from about 300 to about 400 nm, from about 350 to about 450 nm, from about 400 to about 500 nm, from about 400 to about 600 nm, from about 450 to about 650 nm, from about 600 to about 700 nm, from about 650 to about 750 nm, or from about 700 to about 800 nm.

In some embodiments, the light-accepting molecule or combination of light-accepting molecules is present in an amount of from about 0.001 to about 40% by weight of the total composition. In some embodiments, the light-accepting molecule or combination of light-accepting molecules is present in an amount of from about 0.005 to about 2%, from about 0.01 to about 1%, from about 0.01 to about 2%, from about 0.05 to about 1%, from about 0.05 to about 2%, from about 0.1 to about 1%, from about 0.1 to about 2%, from about 1-5%, from about 2.5 to about 7.5%, from about 5 to about 10%, from about 7.5 to about 12.5%, from about 10 to about 15%, from about 12.5 to about 17.5%, from about 15 to 20%, from about 17.5 to about 22.5%, from about 20 to about 25%, from about 22.5 to about 27.5%, from about 25 to about 30%, from about 27.5 to about 32.5%, from about 30 to about 35%, from about 32.5 to about 37.5%, or from about 35 to about 40% by weight of the total composition. In some embodiments, the light-accepting molecule or combination of light-accepting molecules is present in an amount of at least about 0.2% by weight of the total composition.

In some embodiments, the light-accepting molecule or combination of light-accepting molecules is present in an amount of 0.001% to 40% by weight of the total composition. In some embodiments, the light-accepting molecule or combination of light-accepting molecules is present in an amount of from about 0.005% to about 2%, from about 0.01% to about 1%, from about 0.01% to about 2%, from about 0.05% to about 1%, from about 0.05 to about 2%, from about 0.1% to about 1%, from about 0.1% to about 2%, from about 1% to about 5%, from about 2.5% to about 7.5%, from about 5% to about 10%, from about 7.5% to about 12.5%, from about 10% to about 15%, from about 12.5% to about 17.5%, from about 15% to about 20%, from about 17.5% to about 22.5%, from about 20% to about 25%, from about 22.5% to about 27.5%, from about 25% to about 30%, from about 27.5% to about 32.5%, from about 30% to about 35%, from about 32.5% to about 37.5%, or from about 35% to about 40% by weight of the total composition. In some embodiments, the light-accepting molecule or combination of light-accepting molecules is present in an amount of at least about 0.2% by weight of the total composition.

It will be appreciated to those skilled in the art that optical properties of a particular light-accepting molecule may vary depending on the light-accepting molecule's surrounding medium. Therefore, as used herein, a particular light-accepting molecule's absorption and/or emission wavelength (or spectrum) corresponds to the wavelengths (or spectra) measured in a biophotonic composition of the present disclosure.

In some embodiments, the biophotonic compositions disclosed herein may include at least one additional light-accepting molecule. Combining light-accepting molecules may increase photo-absorption by the combined dye molecules and enhance absorption and photo-biomodulation selectivity. This creates multiple possibilities of generating new photosensitive, and/or selective light-accepting molecules.

In some embodiments, the biophotonic topical composition of the present disclosure further comprises an acceptor, or a second, light-accepting molecule. In some embodiments, the donor, or first, light-accepting molecule has an emission spectrum that overlaps at least about 80%, about 70%, about 60%, about 50%, about 40%, about 30%, about 20%, or about 10% with an absorption spectrum of the second light-accepting molecule. In some embodiments, the first light-accepting molecule has an emission spectrum that overlaps at least about 20% with an absorption spectrum of the second light-accepting molecule. In some embodiments, the first light-accepting molecule has an emission spectrum that overlaps at least between 1-10%, at least between 5-15%, at least between 10-20%, at least between 15-25%, at least between 20-30%, at least between 25-35%, at least between 30-40%, at least between 35-45%, at least between 50-60%, at least between 55-65% or at least between 60-70% with an absorption spectrum of the second light-accepting molecule.

In some embodiments, the second light-accepting molecule absorbs at a wavelength in the range of the visible spectrum. In some embodiments, the second light-accepting molecule has an absorption wavelength that is relatively longer than that of the first light-accepting molecule within the range of between about 50-250 nm, between about 25-150 nm or between about 10-100 nm.

As discussed above, the application of light to the compositions of the present disclosure can result in a cascade of energy transfer between the light-accepting molecules. In some embodiments, such a cascade of energy transfer provides photons that penetrate the epidermis, dermis and/or mucosa of the target tissue.

In some embodiments, the light-accepting molecule or light-accepting molecules are selected such that their emitted fluorescent light, on photostimulation, is within one or more of the green, yellow, orange, red and infrared portions of the electromagnetic spectrum, for example having a peak wavelength within the range of about 490 nm to about 800 nm. In some embodiments, the emitted fluorescent light has a power density of between 0.005 to about 10 mW/cm$^2$ or about 0.5 to about 5 mW/cm$^2$.

Suitable light-accepting molecules useful in the biophotonic topical compositions, methods, and uses of the present disclosure include, but are not limited to the following:

The xanthene derivative dyes have been used and tested for a long time worldwide. They display low toxicity and increased fluorescence. The xanthene group consists of three sub-groups: a) the fluorenes; b) fluorones; and c) the rhodoles, any of which may be suitable for the biophotonic compositions, methods, and uses of the present disclosure.

The fluorenes group comprises the pyronines (e.g., pyronine Y and B) and the rhodamines (e.g., rhodamine B, G and WT). Depending on the concentration used, both pyronines and rhodamines may be toxic and their interaction with light may lead to increased toxicity. Similar effects are known to occur for the rhodole dye group.

The fluorone group comprises the fluorescein dye and the fluorescein derivatives.

Fluorescein is a fluorophore commonly used in microscopy with an absorption maximum of about 494 nm and an emission maximum of about 521 nm. The disodium salt of fluorescein is known as D&C Yellow 8. It has very high fluorescence but photodegrades quickly. In the present composition, mixtures of fluorescein with other photostimulators such as indocyanin green and/or saffron red powder will confer increased photoabsorption to these other compounds.

The eosins group comprises Eosin Y (tetrabromofluorescein, acid red 87, D&C Red 22), a light-accepting molecule with an absorption maximum of from about 514 to about 518 nm that stains the cytoplasm of cells, collagen, muscle fibers and red blood cells intensely red; and Eosin B (acid red 91, eosin scarlet, dibromo-dinitrofluorescein), with the same staining characteristics as Eosin Y. Eosin Y and Eosin B are collectively referred to as "Eosin," and use of the term "Eosin" refers to either Eosin Y, Eosin B or a mixture of both. Eosin Y, Eosin B, or a mixture of both can be used because of their sensitivity to the light spectra used: broad spectrum blue light, blue to green light and green light.

In some embodiments, the composition includes in the range of less than about 12% by weight of the total composition of at least one of Eosin B or Eosin Y or a combination thereof. In some embodiments, at least one of Eosin B or Eosin Y or a combination thereof is present from about 0.001% to about 12%, or between about 0.01% and about 1.2%, or from about 0.01% to about 0.5%, or from about 0.01% to about 0.05%, or from about 0.1% to about 0.5%, or from about 0.5% to about 0.8% by weight of the total composition. In some embodiments, at least one of Eosin B or Eosin Y or a combination thereof is present is an amount of about 0.005% by weight of the total composition. In some embodiments, at least one of Eosin B or Eosin Y or a combination thereof is present is an amount of about 0.01% by weight of the total composition. In some embodiments, at least one of Eosin B or Eosin Y or a combination thereof is present is an amount of about 0.02% by weight of the total composition. In some embodiments, at least one of Eosin B or Eosin Y or a combination thereof is present is an amount of about 0.05% by weight of the total composition. In some embodiments, at least one of Eosin B or Eosin Y or a combination thereof is present is an amount of about 0.1% by weight of the total composition. In some embodiments, at least one of Eosin B or Eosin Y or a combination thereof is present is an amount of about 0.2% by weight of the total composition. In some embodiments, at least one of Eosin B or Eosin Y or a combination thereof is present is an amount of at least about 0.2% by weight of the total composition but less than about 1.2% by weight of the total composition. In some embodiments, at least one of Eosin B or Eosin Y or a combination thereof is present is an amount of at least about 0.01% by weight of the total composition but less than about 12% by weight of the total composition.

In some embodiments, the composition includes in the range of less than 12% by weight of the total composition of at least one of Eosin B or Eosin Y or a combination thereof. In some embodiments, at least one of Eosin B or Eosin Y or a combination thereof is present from 0.001% to 12%, or from 0.01% to 1.2%, or from 0.01% to 0.5%, or from 0.1% to 0.5%, or from 0.5% to 0.8%, or from 0.01% to 0.05%, by weight of the total composition. In some embodiments, at least one of Eosin B or Eosin Y or a combination thereof is present is an amount of 0.005% by weight of the total composition. In some embodiments, at least one of Eosin B or Eosin Y or a combination thereof is present is an amount of 0.01% by weight of the total composition. In some embodiments, at least one of Eosin B or Eosin Y or a combination thereof is present is an amount of 0.02% by weight of the total composition. In some embodiments, at least one of Eosin B or Eosin Y or a combination thereof is present is an amount of 0.05% by weight of the total composition. In some embodiments, at least one of Eosin B or Eosin Y or a combination thereof is present is an amount of 0.1% by weight of the total composition. In some embodiments, at least one of Eosin B or Eosin Y or a combination thereof is present is an amount of 0.2% by weight of the total composition. In some embodiments, at least one of Eosin B or Eosin Y or a combination thereof is present is an amount of at least 0.2% by weight of the total composition but less than 1.2% by weight of the total composition. In some embodiments, at least one of Eosin B or Eosin Y or a combination thereof is present is an amount of at least 0.01% by weight of the total composition but less than 12% by weight of the total composition.

Phloxine B (2,4,5,7 tetrabromo 4,5,6,7,tetrachlorofluorescein, D&C Red 28, acid red 92) is a red dye derivative of fluorescein which is used for disinfection and detoxification of waste water through photooxidation. It has an absorption maximum of 535-548 nm. It is also used as an intermediate for making photosensitive dyes and drugs.

Erythrosine B, or simply Erythrosine or Erythrosin (acid red 51, tetraiodofluorescein) is a cherry-pink, coal-based fluorine food dye used as a biological stain, and a biofilm and dental plaque disclosing agent, with a maximum absorbance of 524-530 nm in aqueous solution. It is subject to photodegradation. Erythrosine is also used in some embodiments due to its photosensitivity to the light spectra used and its ability to stain biofilms. In embodiments, the composition includes in the range of less than about 2% by weight Erythrosine B. In some embodiments, Erythrosine B is present in an amount from about 0.005 to about 2%, or from about 0.005% to about 1%, or about 0.01% to about 1% by weight of the total composition. In some embodiments, Erythrosine B is present in an amount of about 0.005% and about 0.15% by weight of the total composition.

Rose Bengal (4,5,6,7 tetrachloro 2,4,5,7 tetraiodofluorescein, acid red 94) is a bright bluish-pink fluorescein derivative with an absorption maximum of 544-549 nm, that has been used as a dye, biological stain and diagnostic aid. Rose Bengal is also used in synthetic chemistry to generate singlet oxygen from triplet oxygen.

Merbromine (mercurochrome) is an organo-mercuric disodium salt of fluorescein with an absorption maximum of 508 nm. It is used as an antiseptic.

The azo (or diazo-) dyes share the N—N group, called azo the group. They are used mainly in analytical chemistry or as food colorings and are not fluorescent. Suitable azo dyes for the compositions, methods, and uses of the disclosure include: Methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

Dye molecules commonly used in staining protocols for biological materials can also be used as photostimulators for the compositions, methods, and uses of the disclosure. Suitable biological stains include, but not limited to:

Saffranin (Saffranin 0, basic red 2) is an azo-dye and is used in histology and cytology. It is a classic counter stain in a Gram stain protocol.

Fuchsin (basic or acid) (rosaniline hydrochloride) is a magenta biological dye that can stain bacteria and has been used as an antiseptic. It has an absorption maximum of 540-555 nm.

3,3'-dihexylocarbocyanine iodide (DiOC6) is a fluorescent dye used for staining the endoplasmic reticulum, vesicle membranes and mitochondria of cells. It shows photodynamic toxicity; when exposed to blue light, has a green fluorescence.

Carminic acid (acid red 4, natural red 4) is a red glucosidal hydroxyanthrapurin naturally obtained from cochineal insects.

Indocyanin green (ICG) is used as a diagnostic aid for blood volume determination, cardiac output, or hepatic function. ICG binds strongly to red blood cells and when used in mixture with fluorescein, it increases the absorption of blue to green light.

Carotenoid dyes are also photostimulators that are useful in the compositions, methods, and uses of the disclosure.

Saffron red powder is a natural carotenoid-containing compound. Saffron is a spice derived from crocus sativus. It is characterized by a bitter taste and iodoform or hay-like fragrance; these are caused by the compounds picrocrocin and saffranal. It also contains the carotenoid dye crocin that gives its characteristic yellow-red color.

Saffron contains more than 150 different compounds, many of which are carotenoids: mangicrocin, reaxanthine, lycopene, and various α and β-carotenes, which show good absorption of light and beneficial biological activity. Also saffron can act as both a photon-transfer agent and a healing factor. Saffron color is primarily the result of a-crocin (8,8 diapo-8,8-carotenoid acid). Dry saffron red powder is highly sensitive to fluctuating pH levels and rapidly breaks down chemically in the presence of light and oxidizing agents. It is more resistant to heat. Data show that saffron has anticarcinogenic, immunomodulating and antioxidant properties. For absorbance, the crocin specific photon wavelength is 440 nm (blue light). It has a deep red colour and forms crystals with a melting point of 186° C.

Crocetin, another compound of saffron, was found to express an antilipidemic action and promote oxygen penetration in different tissues. More specifically, an increased oxygenation of the endothelial cells of the capillaries was observed. Additionally, an increase of the oxygenation of muscles and cerebral cortex was observed and led to an improved survival rate in laboratory animals with induced hemorrhagic shock or emphysema.

Anatto, a spice, contains as main constituent (70-80%) the carotenoid bixin which displays relevant antioxidative properties. β-carotene, also displays suitable characteristics.

Fucoxanthine is a constituent of brown algae with a pronounced ability for photosensitization of redox reactions.

Examples of chlorophyll dyes that are useful in the compositions, methods, and uses of the disclosure, include but are not limited to chlorophyll a, chlorophyll b, oil soluble chlorophyll, bacteriochlorophyll a, bacteriochlorophyll b, bacteriochlorophyll c, bacteriochlorophyll d, protochlorophyll, protochlorophyll a, amphiphilic chlorophyll derivative 1, and amphiphilic chlorophyll derivative 2.

In some aspects of the disclosure, the one or more light-accepting molecules of the biophotonic composition disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2 (Saffranin O), Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid (acid red 4), Celestine blue B, China blue, Cochineal, Celestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, DiOC6, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta 0, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, phycobilins, Phycocyanins, Phycoerythrins. Phycoerythrincyanin (PEC), Phthalocyanines, Picric acid, Ponceau 2R, Ponceau 6R, Ponceau B, Ponceau de Xylidine, Ponceau S, Primula, Purpurin, Pyronin B, Pyronin G, Pyronin Y, Rhodamine B, Rosanilin, Rose bengal, Saffron, Safranin O, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Water blue I, Water soluble eosin, Xylidine ponceau, Yellowish eosin.

In some embodiments, the biophotonic compositions of this disclosure comprise Eosin as a first light-accepting molecule. In some aspects of this embodiment, the Eosin is Eosin Y. In some embodiments, the composition comprises Eosin Y as a first light-accepting molecule and any one or more of Rose Bengal, Erythrosin, Phloxine B as a second light-accepting molecule. It is believed that these combinations have a synergistic effect as Eosin Y can transfer energy to Rose Bengal, Erythrosin or Phloxine B when activated.

In some embodiments, the biophotonic compositions of this disclosure comprise the following synergistic combinations: Eosin Y and Fluorescein; Fluorescein and Rose Bengal; Eosin Y and Rose Bengal; Erythrosine in combination with one or more of Eosin Y, Rose Bengal or Fluorescein; or Phloxine B in combination with one or more of Eosin Y, Rose Bengal, Fluorescein and Erythrosine.

By means of synergistic effects of the light-accepting molecule combinations in the composition, light-accepting molecules which cannot normally be activated by an activating light (such as a blue light from an LED) can be activated through energy transfer from light-accepting molecules which are activated by the activating light. In this way, the different properties of photostimulated light-accepting molecules can be harnessed and tailored according to the cosmetic or the medical therapy required.

For example, Rose Bengal can generate a high yield of singlet oxygen when photostimulated in the presence of molecular oxygen, however, it has a low quantum yield in terms of emitted fluorescent light. Rose Bengal has a peak absorption at approximately 540 nm; so it is normally activated by green light. Eosin Y has a high quantum yield and can be activated by blue light. By combining Rose Bengal with Eosin Y, one obtains a composition which can emit therapeutic fluorescent light and generate singlet oxygen when activated by blue light. In this case, the blue light photostimulates Eosin Y, which transfers some of its energy to Rose Bengal and emits some energy as fluorescence.

Light-accepting molecule combinations can also have a synergistic effect in terms of their photostimulated state. In some embodiments, two light-accepting molecules may be used, one of which emits fluorescent light when activated in the blue and green range, and the other which emits fluorescent light in the red, orange and yellow range, thereby complementing each other and irradiating the target tissue with a broad wavelength of light having different depths of penetration into target tissue.

According to some embodiments, the biophotonic compositions of the present disclosure may further comprise one or more healing factors. Healing factors include compounds that promote or enhance the healing or regenerative process of the tissues on the application site of the composition. During the photostimulation of the composition, there is an increase of the absorption of molecules at the treatment site. An augmentation in the blood flow at the site of treatment is observed for an extended period of time. An increase in the lymphatic drainage and a possible change in the osmotic equilibrium due to the dynamic interaction of the free radical cascades can be enhanced or even fortified with the inclusion of healing factors. In some embodiments, the biophotonic compositions of the present disclosure comprises one or more healing factors selected from, but not limited to, hyaluronic acid, glucosamine, allantoin, or saffron.

Suitable healing factors for the biophotonic compositions, methods and uses of the present disclosure include, but are not limited to:

Hyaluronic acid (hyaluronan or hyaluronate) is a non-sulfated glycosaminoglycan, distributed widely throughout connective, epithelial and neural tissues. It is one of the primary components of the extracellular matrix, and contributes significantly to cell proliferation and migration. Hyaluronan is a major component of the skin, where it is involved in tissue repair. While it is abundant in extracellular matrices, it contributes to tissue hydrodynamics, movement and proliferation of cells and participates in a wide number of cell surface receptor interactions, notably those including primary receptor CD44. The hyaluronidase enzymes degrade hyaluronan and there are at least seven types of hyaluronidase-like enzymes in humans, several of which are tumor suppressors. The degradation products of hyaluronic acid, the oligosaccharides and the very-low molecular weight hyaluronic acid, exhibit pro-angiogenic properties. In addition, recent studies show that hyaluronan fragments, but not the native high molecular mass of hyaluronan, can induce inflammatory responses in macrophages and dendritic cells in tissue injury. Hyaluronic acid is well suited to biological applications targeting the skin. Due to its high biocompatibility, it is used to stimulate tissue regeneration. Current studies evidenced hyaluronic acid appearing in the early stages of healing to physically create room for white blood cells that mediate the immune response. It is used in the synthesis of biological scaffolds for wound healing applications and in wrinkle treatment. In certain embodiments, the composition includes hyaluronic acid in the range of less than about 2% by weight of the total composition hyaluronic acid. In some embodiments, hyaluronic acid is present in an amount from about 0.001% to about 2%, or from about 0.002% to about 2%, or from about 0.002% to about 1% by weight of the total composition.

Glucosamine is one of the most abundant monosaccharides in human tissues and a precursor in the biological synthesis of glycosylated proteins and lipids. It is commonly used in the treatment of osteoarthritis. The common form of glucosamine used is its sulfate salt. Glucosamine shows a number of effects, including anti-inflammatory activity, stimulation of the synthesis of proteoglycans and the synthesis of proteolytic enzymes. A suitable range of concentration over which glucosamine can be used in the present composition is from less than about 5% by weight of the total composition. In some embodiments, glucosamine is present in an amount from about 0.0001% to about 5%, or from about 0.0001% to about 3%, or from about 0.001% to about 3%, or from about 0.001% to about 1%, or from about 0.01% to about 1%, or from about 1% to about 3% by weight of the total composition.

Allantoin is a diureide of glyosilic acid. It has keratolytic effect, increases the water content of the extracellular matrix, enhances the desquamation of the upper layers of dead (apoptotic) skin cells, and promotes skin proliferation and wound healing. In certain embodiments, the composition includes in the range of less than about 1% by weight of the total composition allantoin. In some embodiments, allantoin is present in an amount of from about 0.001% to about 1%, or from about 0.002% to about 1%, or from about 0.02% to about 1%, or from about 0.02% to about 0.5% by weight of the total composition.

In some embodiments, the biophotonic compositions of the present disclosure may further comprise one or more chelating factors. Chelating agents can be included to promote smear layer removal in closed pockets and difficult to reach lesions. Chelating agents act as a metal ion quencher and as a buffer. In some embodiments, the biophotonic compositions of the present disclosure comprise a chelating factor selected from, but not limited to, ethylenediaminotetraacetic acid (EDTA) or ethylene glycol tetraacetic acid (EGTA.

In some embodiments, the biophotonic compositions of the present disclosure may further comprise one or more gelling agents. The gelling agent may be an agent capable of forming a cross-linked matrix, including physical and/or chemical cross-links. The gelling agent can be biocompatible, and may be biodegradable. In some embodiments, the gelling agent is able to form a hydrogel or a hydrocolloid. An appropriate gelling agent is one that can form a viscous liquid or a semisolid. In some embodiments, the gelling agent and/or the composition has appropriate light transmission properties. It is also important to select a gelling agent which will allow biophotonic activity of the light-accepting molecule(s). For example, some light-accepting molecules require a hydrated environment in order to fluoresce. The gelling agent may be able to form a gel by itself or in combination with other ingredients such as water or another gelling agent, or when applied to a treatment site, or when illuminated with light.

The gelling agent according to various embodiments of the present disclosure may include, but not be limited to, polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof, polyoxazolines, including poly(methyloxazoline) and poly(ethyloxazoline); silicones, polyvinyl silicates, tetramethoxyorthosilicates, methyltrimethoxyorthosilicates, tetraalkoxyorthosilicates, trialkoxyorthosilicates, pressure sensitive silicone adhesives (such as BioPSA from Dow-Corning), and polyvinylamines.

The gelling agent according to some embodiments of the present disclosure may include a polymer selected from any of synthetic or semi-synthetic polymeric materials, polyacrylate copolymers, cellulose derivatives and polymethyl vinyl ether/maleic anhydride copolymers. In some embodiments, the hydrophilic polymer comprises a polymer that is a high molecular weight (i.e., molar masses of more than about 5,000, and in some instances, more than about 10,000, or about 100,000, or about 1,000,000) and/or cross-linked polyacrylic acid polymer.

In some embodiments, the gelling agent comprises a carbomer. Carbomers are synthetic high molecular weight polymer of acrylic acid that are cross-linked with either allylsucrose or allylethers of pentaerythritol having a molecular weight of about $3 \times 10^6$. The gelation mechanism depends on neutralization of the carboxylic acid moiety to form a soluble salt. The polymer is hydrophilic and produces sparkling clear gels when neutralized. Carbomer gels possess good thermal stability in that gel viscosity and yield value are essentially unaffected by temperature. As a topical product, carbomer gels possess optimum rheological properties. The inherent pseudoplastic flow permits immediate recovery of viscosity when shear is terminated and the high yield value and quick break make it ideal for dispensing. Aqueous solution of Carbopol® is acidic in nature due to the presence of free carboxylic acid residues. Neutralization of this solution cross-links and gelatinizes the polymer to form a viscous integral structure of desired viscosity.

Carbomers are available as fine white powders which disperse in water to form acidic colloidal suspensions (a 1% dispersion has a pH of approximately 3) of low viscosity. Neutralization of these suspensions using a base, for example sodium, potassium or ammonium hydroxides, low molecular weight amines and alkanolamines, results in the formation of translucent gels. Nicotine salts such as nicotine chloride form stable water-soluble complexes with carbomers at about pH 3.5 and are stabilized at an optimal pH of about 5.6.

In some embodiments of the disclosure, the carbomer is Carbopol®. Such polymers are commercially available from B.F. Goodrich or Lubrizol under the designation Carbopol® 71G NF, 420, 430, 475, 488, 493, 910, 934, 934P, 940, 971PNF, 974P NF, 980 NF, 981 NF and the like. Carbopols are versatile controlled-release polymers, as described by Brock (Pharmacotherapy, 14:430-7 (1994), incorporated herein by reference) and Durrani (Pharmaceutical Res. (Supp.) 8:S-135 (1991), incorporated herein by reference), and belong to a family of carbomers which are synthetic, high molecular weight, non-linear polymers of acrylic acid, crosslinked with polyalkenyl polyether. In some embodiments, the carbomer is Carbopol® 974P NF, 980 NF, 5984 EP, ETD 2020NF, Ultrez 10 NF, 934 NF, 934P NF or 940 NF. In some embodiments, the carbomer is Carbopol® 980 NF, ETD 2020 NF, Ultrez 10 NF, Ultrez 21 or 1382 Polymer, 1342 NF, 940 NF. In some embodiments, about 0.05% to about 10%, about 0.5% to about 5%, or about 1% to about 3% by weight of the total composition of a high molecular weight carbopol can be present as the gelling agent. In some embodiments, the biophotonic composition of the disclosure comprises from about 0.05% to about 10%, from about 0.5% to about 5%, or from about 1% to about 3% by weight of the total composition of a high molecular weight carbopol.

In some embodiments, the gelling agent comprises a hygroscopic and/or a hydrophilic material useful for their water attracting properties. The hygroscopic or hydrophilic material may include, but is not limited to, glucosamine, glucosamine sulfate, polysaccharides, cellulose derivatives (hydroxypropyl methylcellulose, hydroxyethyl cellulose, hydroxypropyl cellulose, methylcellulose and the like), non-cellulose polysaccharides (galactomannans, guar gum, carob gum, gum arabic, sterculia gum, agar, alginates and the like), glycosaminoglycan, poly(vinyl alcohol), poly(2-hydroxyethylmethylacrylate), polyethylene oxide, collagen, chitosan, alginate, a poly(acrylonitrile)-based hydrogel, poly(ethylene glycol)/poly(acrylic acid) interpenetrating polymer network hydrogel, polyethylene oxide-polybutylene terephthalate, hyaluronic acid, high-molecular-weight polyacrylic acid, poly(hydroxy ethylmethacrylate), poly(ethylene glycol), tetraethylene glycol diacrylate, polyethylene glycol methacrylate, and poly(methyl acrylate-co-hydroxyethyl acrylate). In some embodiments, the hydrophilic gelling agent is selected from glucose, modified starch, methyl cellulose, carboxymethyl cellulose, propyl cellulose, hydroxypropyl cellulose, carbomers, alginic acid, sodium alginate, potassium alginate, ammonium alginate, calcium alginate, agar, carrageenan, locust bean gum, pectin, and gelatin.

The gelling agent may be protein-based/naturally derived material such as sodium hyaluronate, gelatin or collagen, lipids, or the like. The gelling agent may be a polysaccharide such as starch, chitosan, chitin, agarose, agar, locust bean gum, carrageenan, gellan gum, pectin, alginate, xanthan, guar gum, and the like.

In some embodiments, the composition can include up to about 2% by weight of the final composition of sodium hyaluronate as the single gelling agent. In some embodiments, the composition can include more than about 4% or more than about 5% by weight of the final composition of gelatin as the single gelling agent. In some embodiments, the composition can include up to about 10% or up to about 8% starch as the single gelling agent. In some embodiments, the composition can include more than about 5% or more than about 10% by weight of the total composition of collagen as the gelling agent. In some embodiments, about 0.1% to about 10% or about 0.5% to about 3% by weight of the total composition of chitin can be used as the gelling agent. In some embodiments, about 0.5% to about 5% by weight of the total composition of corn starch or about 5% to about 10% by weight of the total composition of corn starch can be used as the gelling agent. In some embodiments, more than about 2.5 wt % by weight of the total composition of alginate can be used in the composition as the gelling agent. In some embodiments, the percentages by weight percent of the total composition of the gelling agents can be as follows: cellulose gel (from about 0.3% to about 2.0%), konjac gum (from about 0.5% to about 0.7%), carrageenan gum (from about 0.02% to about 2.0%), xanthan gum (from about 0.01% to about 2.0%), acacia gum (from about 3% to about 30%), agar (from about 0.04% to about 1.2%), guar gum (from about 0.1% to about 1%), locust bean gum (from about 0.15% to about 0.75%), pectin (from about 0.1% to about 0.6%), tara gum (from about 0.1% to about 1.0%), polyvinylpyrrolidone (from about 1% to about 5%), sodium polyacrylate (from about 1% to about 10%). Other gelling agents can be used in amounts sufficient to gel the composition or to sufficiently thicken the composition. It will be appreciated that lower amounts of the above gelling agents may be used in the presence of another gelling agent or a thickener.

In some embodiments, the biophotonic composition of the present disclosure may be further encapsulated, e.g., in a membrane. Such a membrane may be transparent, and/or substantially, or fully impermeable. The membrane may be impermeable to liquid but permeable to gases such as air. In some embodiments, the composition may form a membrane that encapsulates the light-accepting molecule(s) of the biophotonic topical composition, where the membrane may be substantially impermeable to liquid and/or gas. The membrane may be formed of one or more lipidic agents, polymers, gelatin, cellulose or cyclodextrins, or the like. In some embodiments, the membrane is translucent or transparent to allow light to infiltrate to and from the light-accepting molecule(s). In some embodiments, the composition is a dendrimer with an outer membrane comprising poly(propylene amine) In some embodiments, the outer membrane comprises gelatin.

According to some embodiments, the biophotonic compositions of the present disclosure may optionally further comprise one or more polyols. Suitable polyols that may be included in the composition include, but are not limited to a diol, a triol, a saccharide, glycerine, butane-1,2,3-triol, butane-1,2,4-triol, hexane-1,2,6-triol, propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol. In some embodiments when the biophotonic composition of the disclosure includes one or more polyols, the polyol is glycerine. In some embodiments when the biophotonic composition of the disclosure includes one or more polyols, the polyol is propylene glycol. In some embodiments when the biophotonic composition of the disclosure includes one or more polyols, the polyol is a combination of glycerine and propylene glycol.

In some embodiments, one or more polyols are present in an amount of about 5-75% by weight of the total composition, such as 5-75% by weight of the total composition. In some embodiments, one or more polyols are present in an amount of about 10-75% by weight of the total composition, such as 10-75% by weight of the total composition. In some embodiments, one or more polyols are present in an amount of about 15-75% by weight of the total composition, such as 15-75% by weight of the total composition. In some embodiments, one or more polyols are present in an amount of about 20-75% by weight of the total composition, such as 20-75% by weight of the total composition.

The biophotonic compositions of the disclosure can also include other ingredients such as humectants (e.g., glycerine, ethylene glycol, and propylene glycol), preservatives (e.g., parabens), pH adjusters (e.g., sodium hydroxide and HCl) and extracts (e.g., rieshi).

In some embodiments, the biophotonic composition of the disclosure comprises one or more salts selected from bicarbonate salts, carbonate salts or a combination of the foregoing salts. In some embodiments, the bicarbonate salts are selected from ammonium bicarbonate, caesium bicarbonate, potassium bicarbonate, sodium bicarbonate, choline bicarbonate, aminoguanidine bicarbonate, or tetraethylammonium bicarbonate. In some embodiments, the carbonate salts are selected from barium carbonate, beryllium carbonate, caesium carbonate, calcium carbonate, cobalt (II) carbonate, copper (II) carbonate, lithium carbonate, magnesium carbonate, nickel (II) carbonate, potassium carbonate, sodium carbonate, or zinc carbonate.

In some embodiments, the biophotonic composition of the disclosure comprises one or more bicarbonate salts. In some embodiments when the biophotonic composition comprises one or more bicarbonate salts, the bicarbonate salt is sodium bicarbonate. In some embodiments when the biophotonic composition comprises one or more bicarbonate salts, the bicarbonate salt is potassium bicarbonate. In some embodiments, the biophotonic composition of the disclosure comprises one or more carbonate salts. In some embodiments when the biophotonic composition comprises one or more carbonate salts, the carbonate salt is sodium carbonate. In some embodiments when the biophotonic composition comprises one or more carbonate salts, the carbonate salt is potassium carbonate. In some embodiments when the biophotonic composition comprises one or more carbonate salts, the carbonate salt is calcium carbonate.

In some embodiments, the one or more salts selected from bicarbonate salts, carbonate salts or a combination of the foregoing salts are present in an amount of about 0.01-30% by weight of the total biophotonic composition. In some embodiments, the one or more salts selected from bicarbonate salts, carbonate salts or a combination of the foregoing salts are present in an amount of about 0.01-20% by weight of the total biophotonic composition. In some embodiments, the one or more salts selected from bicarbonate salts, carbonate salts or a combination of the foregoing salts are present in an amount of about 0.01-10% by weight of the total biophotonic composition. In some embodiments, the one or more salts selected from bicarbonate salts, carbonate salts or a combination of the foregoing salts are present in an amount of about 0.01-5% by weight of the total biophotonic composition. In some embodiments, the one or more salts selected from bicarbonate salts, carbonate salts or a combination of the foregoing salts are present in an amount of about 0.05-30% by weight of the total biophotonic composition. In some embodiments, the one or more salts selected from bicarbonate salts, carbonate salts or a combination of the foregoing salts are present in an amount of about 0.05-20% by weight of the total biophotonic composition. In some embodiments, the one or more salts selected from bicarbonate salts, carbonate salts or a combination of the foregoing salts are present in an amount of about 0.05-10% by weight of the total biophotonic composition. In some embodiments, the one or more salts selected from bicarbonate salts, carbonate salts or a combination of the foregoing salts are present in an amount of about 0.05-5% by weight of the total biophotonic composition. In some embodiments, the one or more salts selected from bicarbonate salts, carbonate salts or a combination of the foregoing salts are present in an amount of about 0.1-30% by weight of the total biophotonic composition. In some embodiments, the one or more salts selected from bicarbonate salts, carbonate salts or a combination of the foregoing salts are present in an amount of about 0.1-20% by weight of the total biophotonic composition. In some embodiments, the one or more salts selected from bicarbonate salts, carbonate salts or a combination of the foregoing salts are present in an amount of about 0.1-10% by weight of the total biophotonic composition.

In some embodiments, the pH of the composition is in or adjusted to the range of about 4 to about 10, such as from about 4 to about 9, from about 4 to about 8, from about 4 to about 7, from about 4 to 6.5, from about 4 to 6, from about 4 to 5.5, from 4 to 5. In some embodiments, the pH of the composition is in or adjusted to the range of from about 4 to about 9. In some embodiments, the pH of the composition is in or adjusted to the range of from about 4 to about 8. In some embodiments, the pH of the composition is within the range of from about 4 to about 7. In some embodiments, the pH of the composition is within the range of about from 4 to about 6.5. In some embodiments, the pH of the composition is within the range of from about 4 to about 6. In some embodiments, the pH of the composition is within the range of from about 4 to about 5.5. In some embodiments, the pH of the composition is within the range of from about 4 to about 5. In some embodiments, the pH of the composition is within the range of about 5.0 to about 8.0, such as from about 6.0 to about 8.0, from about 6.5 to about 7.5, from about 5.5 to about 7.5. In some embodiments, the pH of the composition is within the range of from about 6.0 to about 8.0. In some embodiments, the pH of the composition is within the range of from about 6.5 to about 7.5. In some embodiments, the pH of the composition is within the range of from about 5.5 to about 7.5.

In some embodiments, the pH of the composition is in or adjusted to the range of from 4 to 10, such as from 4 to 9, from 4 to 8, from 4 to 7, from 4 to 6.5, from 4 to 6, from 4 to 5.5, from 4 to 5, from 5.0 to 8.0, from 6.0 to 8.0, from 6.5 to 7.5, from 5.5 to 7.5. In some embodiments, the pH of the composition is in or adjusted to the range of 4 to 9. In some embodiments, the pH of the composition is in or adjusted to the range of 4 to 8. In some embodiments, the pH of the composition is within the range of 4 to 7. In some embodiments, the pH of the composition is within the range of 4 to 6.5. In some embodiments, the pH of the composition is within the range of 4 to 6. In some embodiments, the pH of the composition is within the range of 4 to 5.5. In some embodiments, the pH of the composition is within the range of 4 to 5. In some embodiments, the pH of the composition is within the range of 5.0 to 8.0. In some embodiments, the pH of the composition is within the range of 6.0 to 8.0. In some embodiments, the pH of the composition is within the range of 6.5 to 7.5. In some embodiments, the pH of the composition is within the range of 5.5 to 7.5.

In some embodiments, the biophotonic compositions of the disclosure also include an aqueous substance (such as water) or an alcohol. Alcohols include, but are not limited to, ethanol, propanol, isopropanol, butanol, iso-butanol, t-butanol or pentanol. In some embodiments, the light-accepting molecule or combination of light-accepting molecules is in solution in a medium of the biophotonic composition. In some embodiments, the light-accepting molecule or combination of light-accepting molecules is in solution in a medium of the biophotonic composition, wherein the medium is an aqueous substance.

The biophotonic compositions suitable for use in the methods of the present disclosure may be selected from any of the embodiments of the biophotonic compositions described above. For instance, the biophotonic compositions useful in the method of the present disclosure may comprise a light-accepting molecule, such as a light-accepting molecule that undergoes at least partial photobleaching upon application of light. The light-accepting molecule may absorb at a wavelength of from about 200 nm to about 800 nm, such as, from about 200 nm to about 700 nm, from about 200 nm to about 600 nm or from about 200 nm to about 500 nm. In some embodiments, the light-accepting molecule absorbs at a wavelength of from about 200 nm to about 600 nm. In some embodiments, the light-accepting molecule absorbs light at a wavelength of from about 200 nm to about 300 nm, from about 250 nm to about 350 nm, from about 300 nm to about 400 nm, from about 350 nm to about 450 nm, from about 400 nm to about 500 nm, from about 450 nm to about 650 nm, from about 600 nm to about 700 nm, from about 650 nm to about 750 nm or from about 700 nm to about 800 nm. In some embodiments, suitable biophotonic compositions for the methods of the present disclosure may further comprise at least one additional light-accepting molecule (e.g., a second light-accepting molecule). The absorption spectrum of the second light-accepting molecule overlaps at least about 80%, about 70%, about 60%, about 50%, about 40%, about 30%, or about 20% with the emission spectrum of the first light-accepting molecule. In some embodiments, the first light-accepting molecule has an emission spectrum that overlaps at least about 1-10%, about 5-15%, about 10-20%, about 15-25%, about 20-30%, about 25-35%, about 30-40%, about 35-45%, about 50-60%, about 55-65% or about 60-70% with an absorption spectrum of the second light-accepting molecule.

Illumination of the biophotonic composition with light may cause a transfer of energy from the first light-accepting molecule to the second light-accepting molecule. Subsequently, the second light-accepting molecule may emit energy as fluorescence and/or generate reactive oxygen species. In some embodiments of the methods the present disclosure, energy transfer caused by the application of light is not accompanied by concomitant generation of heat, or does not result in tissue damage.

In the methods of the present disclosure, any source of actinic light can be used to illuminate the biophotonic compositions. Any type of halogen, LED or plasma arc lamp or laser may be suitable. The primary characteristic of suitable sources of actinic light will be that they emit light in a wavelength (or wavelengths) appropriate for activating the one or more photostimulators present in the composition. In some embodiments, an argon laser is used. In some embodiments, a potassium-titanyl phosphate (KTP) laser (e.g., a GreenLight™ laser) is used. In another embodiment, sunlight may be used. In some embodiments, a LED photocuring device is the source of the actinic light. In some embodiments, the source of the actinic light is a source of light having a wavelength from about 200 nm to about 800 nm. In some embodiments, the source of the actinic light is a source of visible light having a wavelength between about 400 nm and about 700 nm. In some embodiments, the source of the actinic light is a source of visible light having a wavelength between about 400 nm and about 600 nm. In some embodiments, the source of the actinic light is a source of visible light having a wavelength between about 400 nm and about 550 nm. In some embodiments, the source of the actinic light is a source of visible light having a wavelength between about 380 nm and about 700 nm. In some embodiments, the source of the actinic light is a source of visible light having a wavelength between about 380 nm and about 600 nm. In some embodiments, the source of the actinic light is a source of visible light having a wavelength between about 380 nm and about 550 nm. In some embodiments, the source of the actinic light is a source of light having a wavelength between 200 nm to 800 nm. In some embodiments, the source of the actinic light is a source of visible light having a wavelength between 400 nm and 700 nm. In some embodiments, the source of the actinic light is a source of visible light having a wavelength between 400 nm and 600 nm. In some embodiments, the source of the actinic light is a source of visible light having a wavelength between 400 nm and 550 nm. In some embodiments, the source of the actinic light is a source of visible light having a wavelength between 380 nm and 700 nm. In some embodiments, the source of the actinic light is a source of visible light having a wavelength between 380 nm and 600 nm. In some embodiments, the source of the actinic light is a source of visible light having a wavelength between 380 nm and 550 nm. In some embodiments, the biophotonic composition of the disclosure is illuminated with violet and/or blue light. Furthermore, the source of actinic light should have a suitable power density. Suitable power density for non-collimated light sources (LED, halogen or plasma lamps) are in the range from about 1 mW/cm$^2$ to about 1200 mW/cm$^2$, such as from about 50 mW/cm$^2$ to about 1000 mW/cm$^2$, from 100 mW/cm$^2$ to about 900 mW/cm$^2$, from 200 mW/cm$^2$ to about 800 mW/cm$^2$, or from about 1 mW/cm$^2$ to about 200 mW/cm$^2$. In some embodiments, suitable power density for non-collimated light sources (LED, halogen or plasma lamps) are in the range from about 1 mW/cm$^2$ to about 200 mW/cm$^2$. In some embodiments, suitable power density for laser light sources is in the range from about 0.5 mW/cm$^2$ to about 0.8 mW/cm$^2$.

In some embodiments of the methods of the present disclosure, the light has an energy at the skin of from about 1 mW/cm$^2$ to about 500 mW/cm$^2$, or about 1-300 mW/cm$^2$, or about 1-200 mW/cm$^2$, wherein the energy applied depends at least on the condition being treated, the wavelength of the light, the distance of the skin from the light source, and the thickness of the biophotonic composition. In some embodiments, the light at the skin is from about 1 to about 40 mW/cm$^2$, or about 20-60 mW/cm$^2$, or about 40-80 mW/cm$^2$, or about 60-100 mW/cm$^2$, or about 80-120 mW/cm$^2$, or about 100-140 mW/cm$^2$, or about 120-160 mW/cm$^2$, or about 140-180 mW/cm$^2$, or about 160-200 mW/cm$^2$, or about 110-240 mW/cm$^2$, or about 110-150 mW/cm$^2$, or about 190-240 mW/cm$^2$.

In some embodiments, the light-accepting molecule or combination of light-accepting molecules can be photostimulated by ambient light which may originate from the sun or other light sources. Ambient light can be considered to be a general illumination that comes from all directions in a room that has no visible source. In some embodiments, the light-accepting molecule or combination of light-accepting molecules can be photostimulated by light in the visible range of the electromagnetic spectrum. Exposure times to ambient light may be longer than that to direct light.

In some embodiments, different sources of light can be used to activate the biophotonic compositions, such as a combination of ambient light and direct LED light.

The duration of the exposure to actinic light required will be dependent on the surface of the treated area, the severity of the condition that is being treated, the power density, wavelength and bandwidth of the light source, the thickness of the biophotonic composition, and the treatment distance from the light source. The illumination of the treated area by fluorescence may take place within seconds or even fragment of seconds, but a prolonged exposure period is beneficial to exploit the synergistic effects of the absorbed, reflected and reemitted light on the composition of the present disclosure and its interaction with the tissue being treated. In some embodiments, the time of exposure to actinic light of the tissue or skin or wound on which the biophotonic composition has been applied is a period from about 1 second to about 60 minutes. In some embodiments, the time of exposure to actinic light of the tissue or skin or wound on which the biophotonic composition has been applied is a period from about 1 minute to about 60 minutes. In some embodiments, the time of exposure to actinic light of the tissue, skin or wound on which the biophotonic composition has been applied is a period from about 1 minute to about 5 minutes. In some embodiments, the time of exposure to actinic light of the tissue, skin or wound on which the biophotonic composition has been applied is a period from about 1 minute and 5 minutes. In another embodiment, the time of exposure is from about 1 second to about 5 minutes or from about 60 seconds to about 5 minutes. In another embodiment, the time of exposure to actinic light of the tissue on which the biophotonic composition has been applied is a period of less than about 5 minutes. In another embodiment, the time of exposure is from about 1 second to about 5 minutes, or from about 60 seconds and about 5 minutes per cm$^2$ of the area to be treated, so that the total time of exposure of a 10 cm$^2$ area would be from 10 minutes and 50 minutes.

In some embodiments, the biophotonic composition is illuminated for a period from about 1 minute to about 3 minutes. In some embodiments, light is applied for a period from about 1 to about 30 seconds, from about 1 to about 60 seconds, from about 15 seconds to about 45 seconds, from about 30 seconds to about 60 seconds, from about 0.75 minute to about 1.5 minutes, from about 1 minute to about 2 minutes, from about 1.5 minute to about 2.5 minutes, from about 2 minutes to about 3 minutes, from about 2.5 minutes to about 3.5 minutes, from about 3 minutes to about 4 minutes, from about 3.5 minutes to about 4.5 minutes, from about 4 minutes to about 5 minutes, from about 5 minutes to about 10 minutes, from about 10 minutes to about 15 minutes, from about 15 minutes to about 20 minutes, from about 20 minutes to about 25 minutes, or from about 20 minutes to about 30 minutes. In some embodiments, light is applied for a period of about 1 second. In some embodiments, light is applied for a period of about 5 seconds. In some embodiments, light is applied for a period of about 10 seconds. In some embodiments, light is applied for a period of about 20 seconds. In some embodiments, light is applied for a period of about 30 seconds. In some embodiments, the biophotonic composition is illuminated for a period less than about 60 minutes. In some embodiments, the biophotonic composition is illuminated for a period less than about 30 minutes. In some embodiments, the biophotonic composition is illuminated for a period less than about 20 minutes. In some embodiments, the biophotonic composition is illuminated for a period less than about 15 minutes. In some embodiments, the biophotonic composition is illuminated for a period less than about 10 minutes. In some embodiments, the biophotonic composition is illuminated for a period less than about 5 minutes. In some embodiments, the biophotonic composition is illuminated for a period less than about 1 minute. In some embodiments, the biophotonic composition is illuminated for a period less than about 30 seconds. In some embodiments, the biophotonic composition is illuminated for a period less than about 20 seconds. In some embodiments, the biophotonic composition is illuminated for a period less than about 10 seconds. In some embodiments, the biophotonic composition is illuminated for a period less than about 5 seconds. In some embodiments, the biophotonic composition is illuminated for a period less than about 1 second. In some embodiments, the source of actinic light is in continuous motion over the treated area for the appropriate time of exposure. In some embodiments, multiple applications of the biophotonic composition and actinic light are performed. In some embodiments, the tissue, skin or wound is exposed to actinic light at least two, three, four, five or six times. In some embodiments, the tissue, skin or wound is exposed to actinic light at least two, three, four, five or six times with a resting period in between each exposure. In certain such embodiments, the resting period is less than about 1 minute, less than about 5 minutes, less than about 10 minutes, less than about 20 minutes, less about 40 minutes, less than about 60 minutes, less than about 2 hours, less than about 4 hours, less about 6 hours, or less than 12 hours. In some embodiments, the entire treatment may be repeated in its entirety as may be required by the patient. In some embodiments, a fresh application of the biophotonic composition is applied before another exposure to actinic light.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

The examples below are given so as to illustrate the practice of various embodiments of the present technology. They are not intended to limit or define the entire scope of this technology. It should be appreciated that the technology is not limited to the particular embodiments described and illustrated herein but includes all modifications and variations falling within the scope of the disclosure as defined in the appended embodiments.

Example 1: Testing Effects of Photostimulated Biophotonic Compositions on Energy Emission of Biological Tissue Ultra-weak photon emission is low-level chemiluminescence from biological systems generated in all living organisms, including humans, during the oxidative metabolic and stress processes. Low-noise photomultiplier tube (PMT) and highly sensitive charge coupled device (CCD) camera make it possible to monitor spontaneous ultra-weak photon emission. One-dimensional detection of ultra-weak photon emission uses low-noise PMT whereas two-dimensional imaging of ultra-weak photon emission uses highly sensitive CCD camera. The aim of this experiment was to measure spontaneous ultra-weak photon emission from skin samples by performing the following measurement assays:

One-dimensional kinetics of ultra-weak photon emission induced by a multi-LED lamp in the presence of biophotonic compositions of the present disclosure;

Two-dimensional imaging of ultra-weak photon emission induced by multi-LED lamp (blue light source);

Two-dimensional imaging of ultra-weak photon emission induced by multi-LED lamp in the presence of biophotonic compositions of the present disclosure;

One-dimensional kinetics of ultra-weak photon emission induced by visible light in the presence of biophotonic compositions of the present disclosure comprising light-accepting molecules;

UVA induced ultra-weak photon emission imaging from skin sample; and

UVA induced ultra-weak photon emission imaging from skin sample in the presence of biophotonic compositions of the present disclosure comprising light-accepting molecules.

Porcine skin which bears similar histological and physiological properties to live human skin was chosen for testing. The vascular anatomy and collagen fiber arrangement in the dermis, as well as the content of the stratum corneum glycolipids and ceramides are similar in human and porcine skin. For the purpose, skin sample (intact pig ear) was transported under standard conditions within 20 min of sacrifice. For each set of measurements, fresh skin sample collected each day was used. Prior to illumination, the following compositions or biophotonic compositions were topically applied to certain portions of the pig's skin:

Assay 1: no topical application;
Assay 2: blank gel (BPG), no urea peroxide (UP), no light-accepting molecule;
Assay 3: biophotonic composition comprising 12% UP, no light-accepting molecule;
Assay 4: biophotonic composition comprising 12% UP, Eosin.

A KLOX™ Multi-LED Lamp was used as multi-LED lamp as per the instructions provided by the manufacturer. The intensity at a distance of 5 cm was measured to be ~2800 µmol photons $m^{-2}s^{-1}$. Wavelength: 415 nm (6 LED's and 446 nm (40 LED)). UVA: Ultraviolet-A (320-400 nm).

Measurement of Ultra-weak photon emission—The CCD camera and the PMT system were placed in a dark insulated chamber (with controlled environmental conditions) located inside a black painted inner dark room (3 m×1.5 m×2.5 m), whereas the control system was monitored from outside the dark room. The door in the inner dark room was protected completely with a black curtain to restrict entry of any external light. A scheme of the experimental setup is presented in FIG. 1A and FIG. 1B.

One-dimensional ultra-weak photon emission kinetic measurements—One-dimensional photon counting was done using low-noise photon counting unit C9744 (Hamamatsu Photonics K.K., Iwata city, Japan) with a spectral sensitivity in the range of 160-710 nm. For reduction of thermal electrons, PMT was cooled down to −30° C. using thermoelectric cooler C9143 (Hamamatsu Photonics, K.K., Iwata city, Japan). The PMT was kept vertically to minimize the dark counts to ~2 counts s−1 at −960 mV.

Two-dimensional photon emission imaging—Highly sensitive CCD camera VersArray 1300B (Princeton instruments, Trenton, NJ, USA) with spectral sensitivity in the range of 200-1000 nm restricted to 350-1000 nm due to the objective lens mounted and almost 30% quantum efficiency in the visible range of the spectrum was used for two-dimensional photon imaging. For reduction of dark current, CCD camera was cooled down to −104° C. using a liquid-nitrogen cooling system. The data correction was made by subtracting the background noise before every measurement. The measurement was done in the image format of 1340×1300 and 335×325 pixels with following CCD camera parameters: scan rate, 100 kHz; gain, 2; accumulation time, 30 min.

Figure 2A:
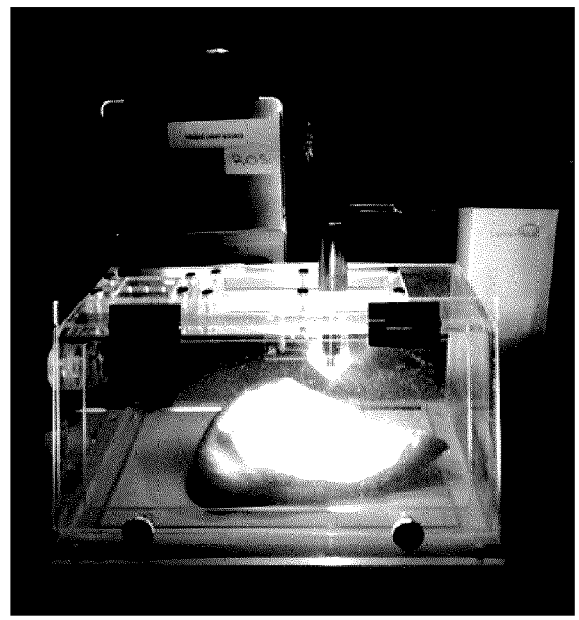
FIGS. 2A-2B are pictures of the setup according to the embodiment of FIGS. 1A-1B.
Figure 2B:

Visible light exposure—As a control, the effect of visible light was tested on a pig's skin sample onto which was applied a biophotonic composition comprising Eosin as chomophore by illumination with a continuous white light (~2800 μmol photons $m^{-2}s^{-1}$). FIG. 2A and FIG. 2B show the experimental set up.

UVA irradiation exposure—The skin sample was exposed to UVA radiation using Philips UVA CLEO SWIFT lamp with a spectral range of 320-400 nm measured by Spectral Radiometer; LICOR LI-1800 (LI-COR Biosciences, St. John's Innovation, Cambridge, UK). The exposure time was kept 5 min. The power density on the skin surface of the hand was approx. 20 $Wm^{-2}$.

Biophotonic formulation application procedure—The biophotonic formulations were prepared and topically applied onto the pig's skin surface as instructed prior to treatment with light source Immediately after the light treatment, the biophotonic formulation was wiped completely from the pig's skin surface and washed with double-distilled $H_2O$ at pH 7.0.

Time lapse—The time between the end of exposure of the pig's skin sample to light with the lamp and start of measurement of emission by the pig's skin was kept at 30 seconds for each assay.

Figure 3A:
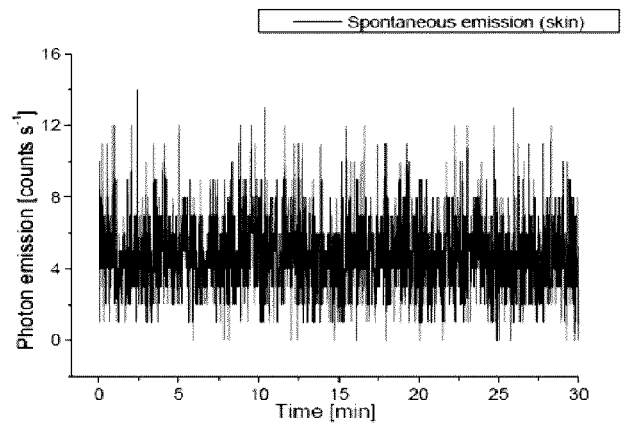
FIGS. 3A-3B are a graph (FIG. 3A) and pictures (FIG. 3B) showing the spontaneous emission of ultra-weak photon from a non-treated pig's skin (no treatment with biophotonic composition).
Figure 3B:
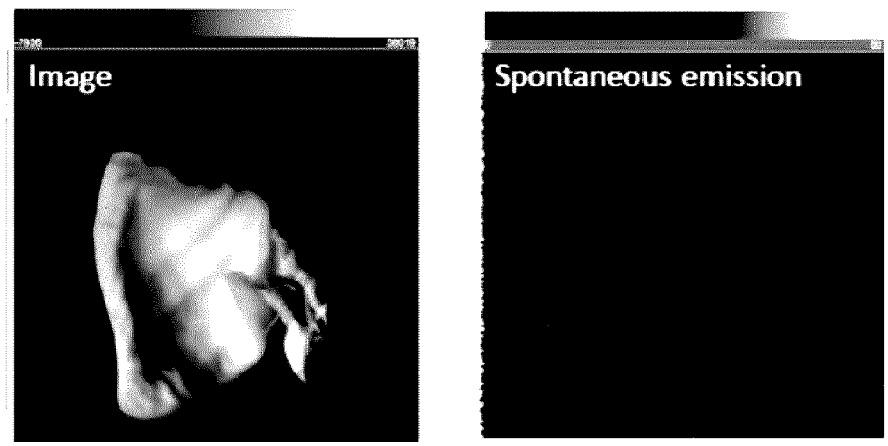
Figure 4A:
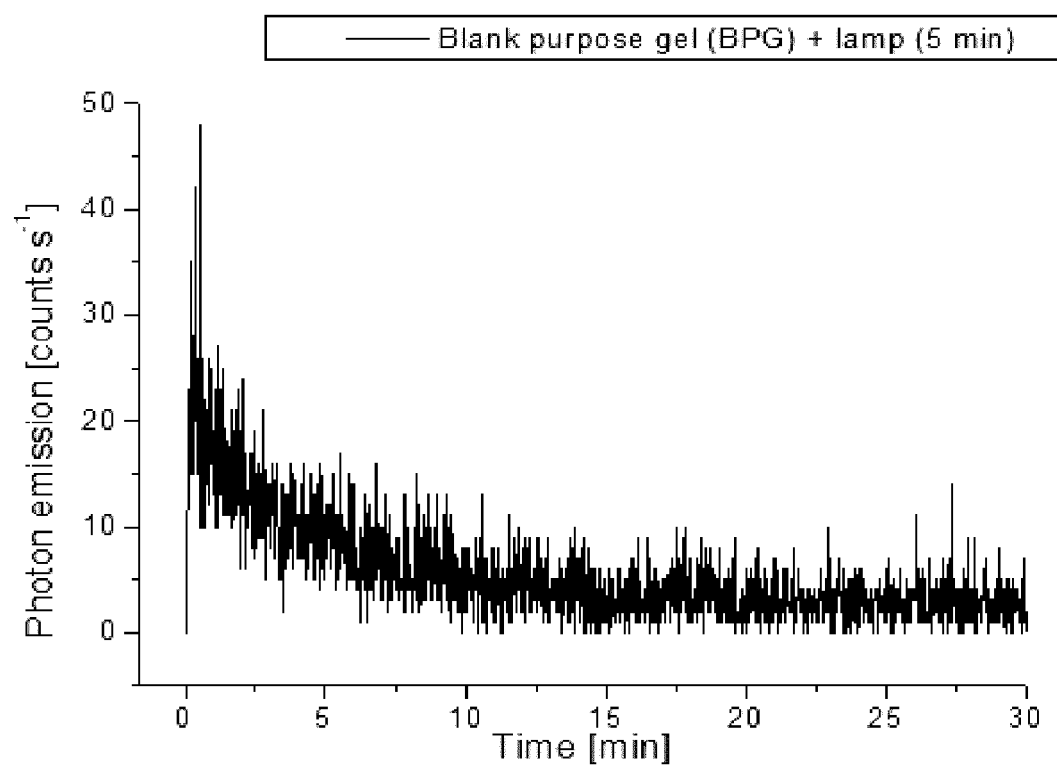
FIGS. 4A-4E are a graph (FIG. 4A) and pictures (FIGS. 4B-4E) showing the emission of ultra-weak photon from a pig's skin (no treatment with biophotonic composition) and illuminated for 5 mins with KLOX™ multi-LED lamp; accumulation time: 30 min.
Figure 4B:
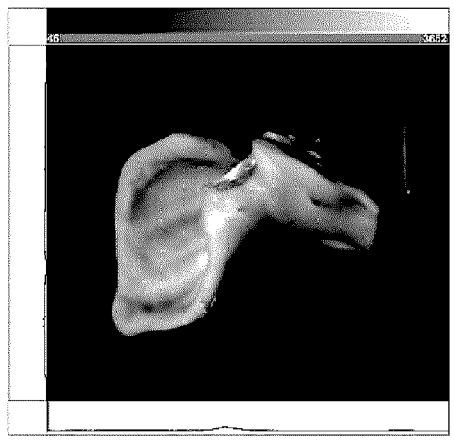
Figure 4C:
Figure 4D:
Figure 4E:

FIG. 3A and FIG. 3B show the spontaneous (basal or control) emission of ultra-weak photon of a non-treated pig's skin not treated with a biophotonic composition prior to illumination.

Assay 1: FIGS. 4A-4E show the emission of ultra-weak photon of a pig's skin onto which no biophotonic composition was applied prior to illumination with KLOX™ multi-LED lamp for 5 minutes.

Figure 5A:
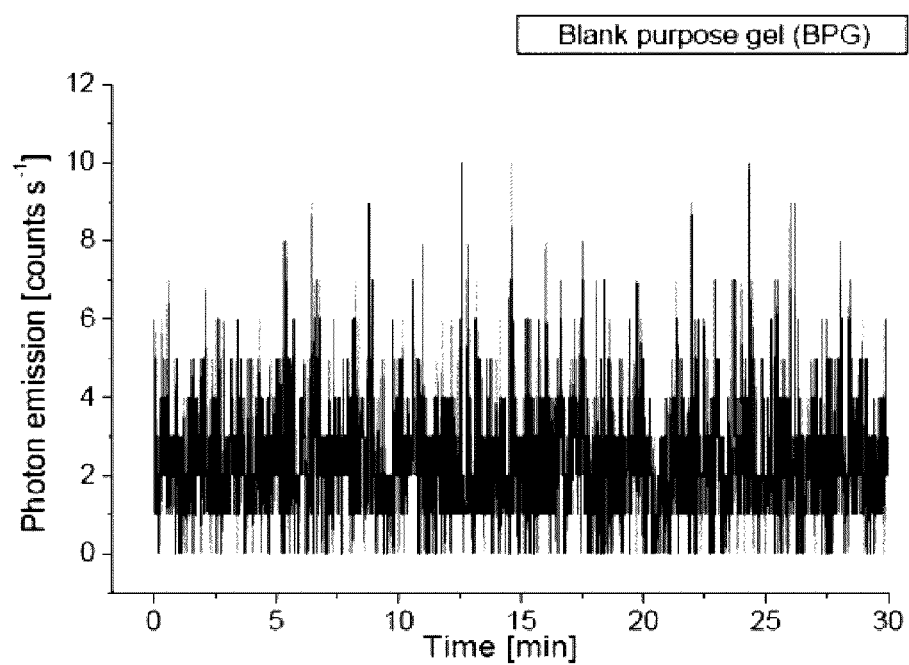
FIGS. 5A-5B are graph (FIG. 5A) and pictures (FIG. 5B) showing the emission of ultra-weak photon from a pig's skin treated with basal (BPG) topical application and illuminated with KLOX™ multi-LED lamp for 5 minutes.
Figure 5B:
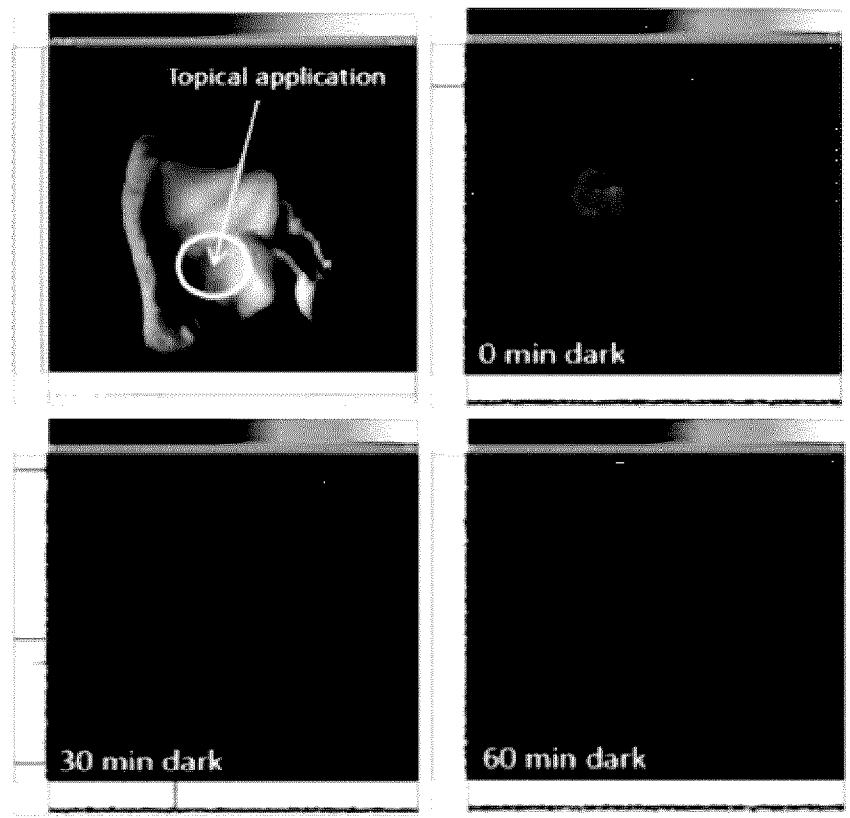

Assay 2: FIGS. 5A-5B show the emission of ultra-weak photon of pig's skin treated with BPG topical application prior to being illuminated with KLOX™ multi-LED lamp for 5 minutes.

Figure 6A:
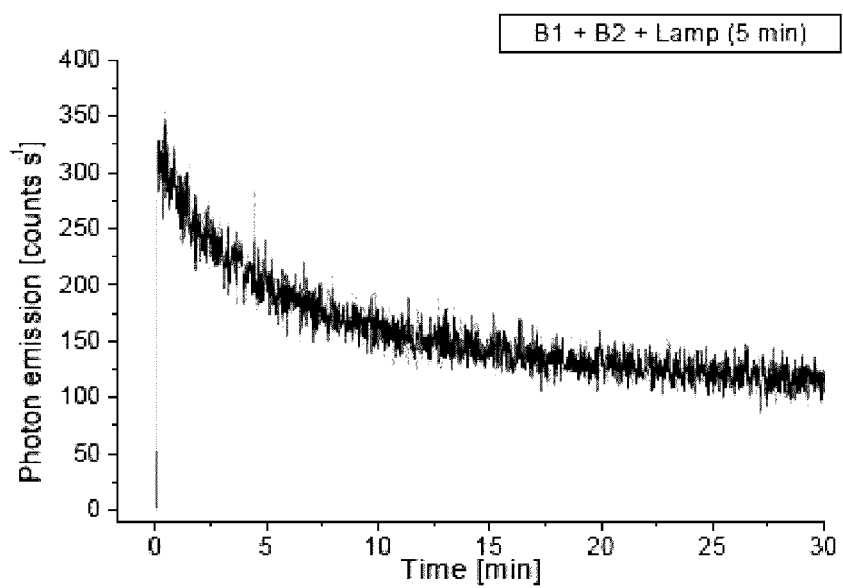
FIGS. 6A-6B are graph (FIG. 6A) and pictures (FIG. 6B) showing the emission of ultra-weak photon from a pig's skin treated with a biophotonic composition according to one embodiment of the present disclosure comprising 12% urea peroxide (UP) and no light-accepting molecule and illuminated with KLOX™ multi-LED lamp for 5 minutes.
Figure 6B:
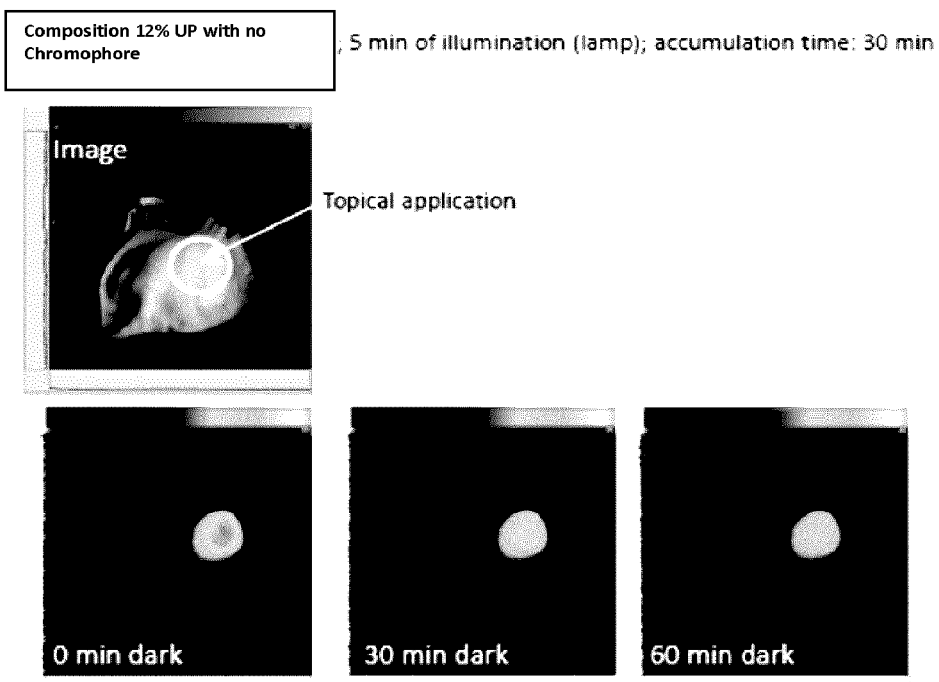

Assay 3: FIGS. 6A-6B show the emission of ultra-weak photon of pig's skin treated with a biophotonic composition comprising 12% UP and no light-accepting molecule prior to being illuminated with KLOX™ multi-LED lamp for 5 minutes.

Figure 7A:
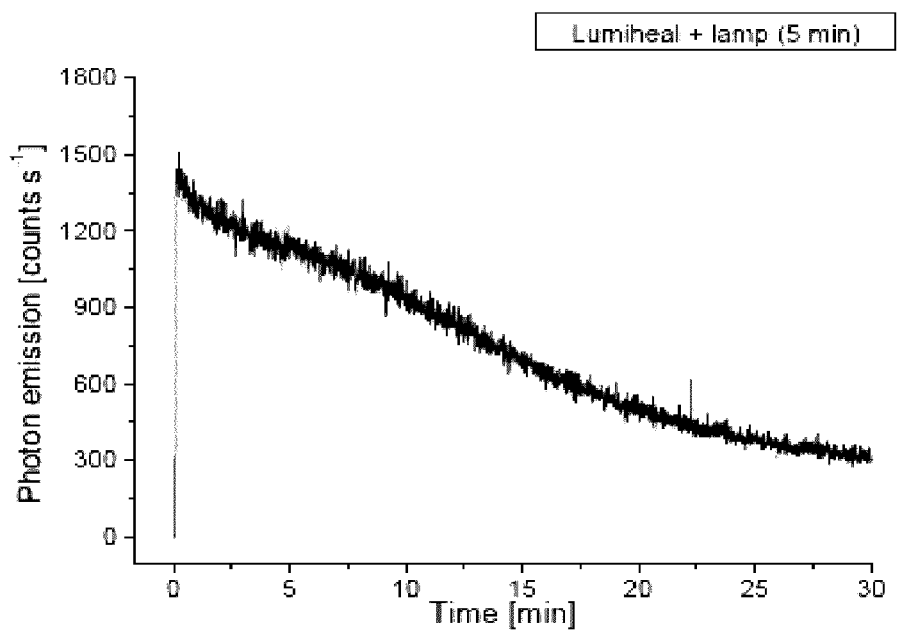
FIGS. 7A-7C are graph (FIG. 7A) and pictures (FIGS. 7B and 7C) showing the emission of ultra-weak photon of a pig's skin treated with a biophotonic composition according to one embodiment of the present disclosure comprising light-accepting molecules and illuminated with KLOX™ multi-LED lamp for 5 minutes.
Figure 7B:
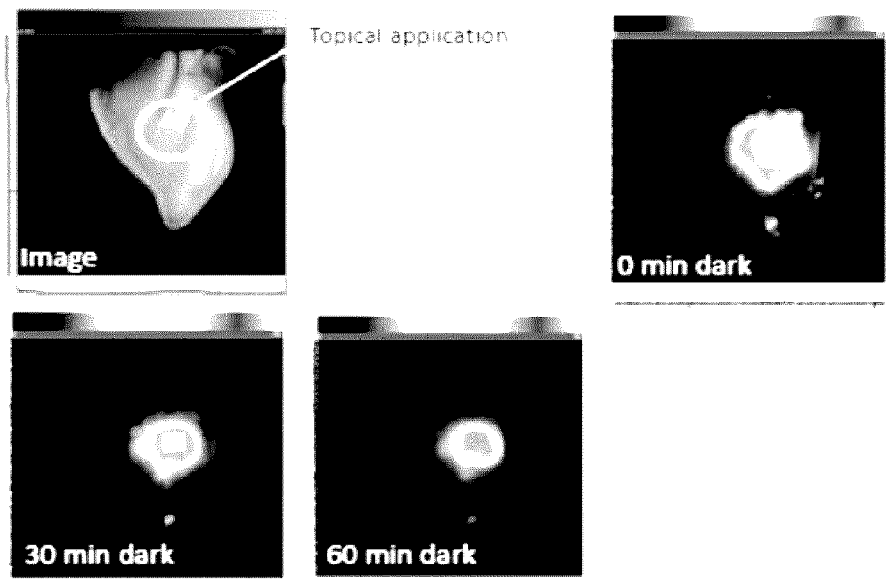
Figure 7C:
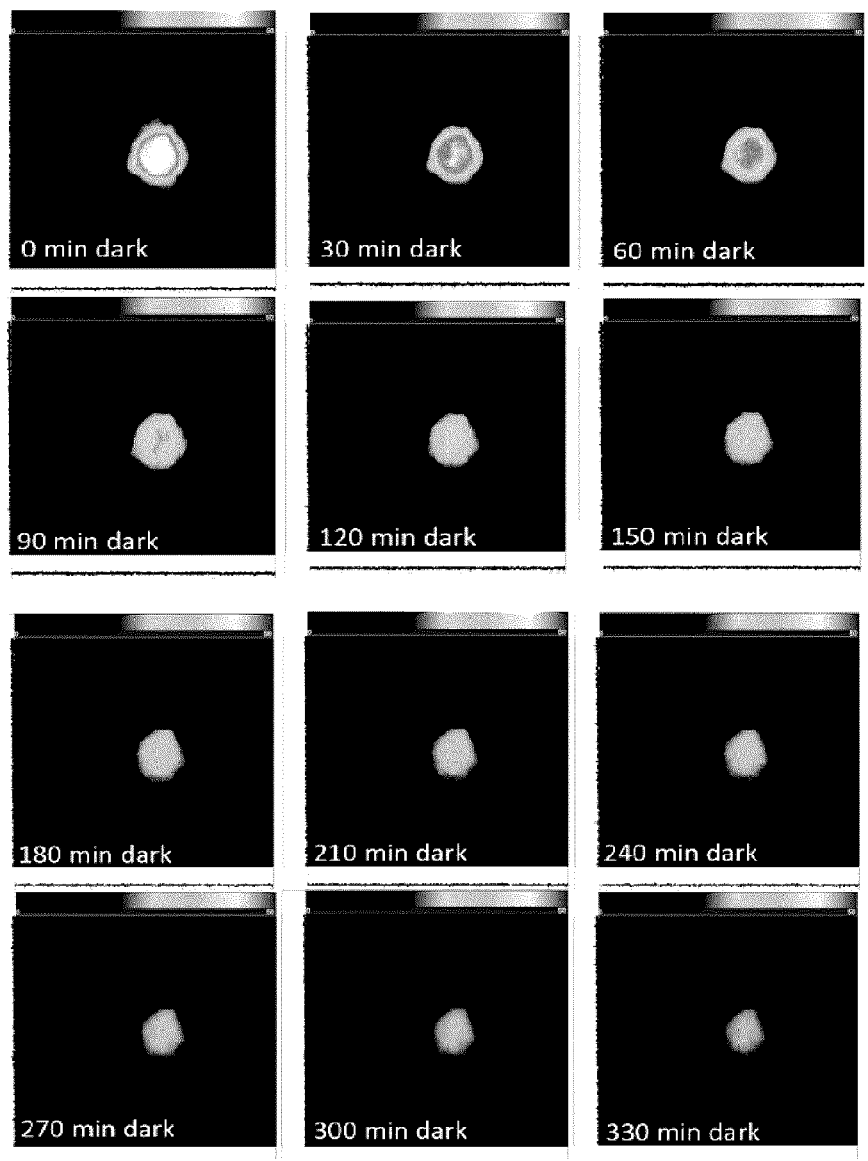
Figure 7C:
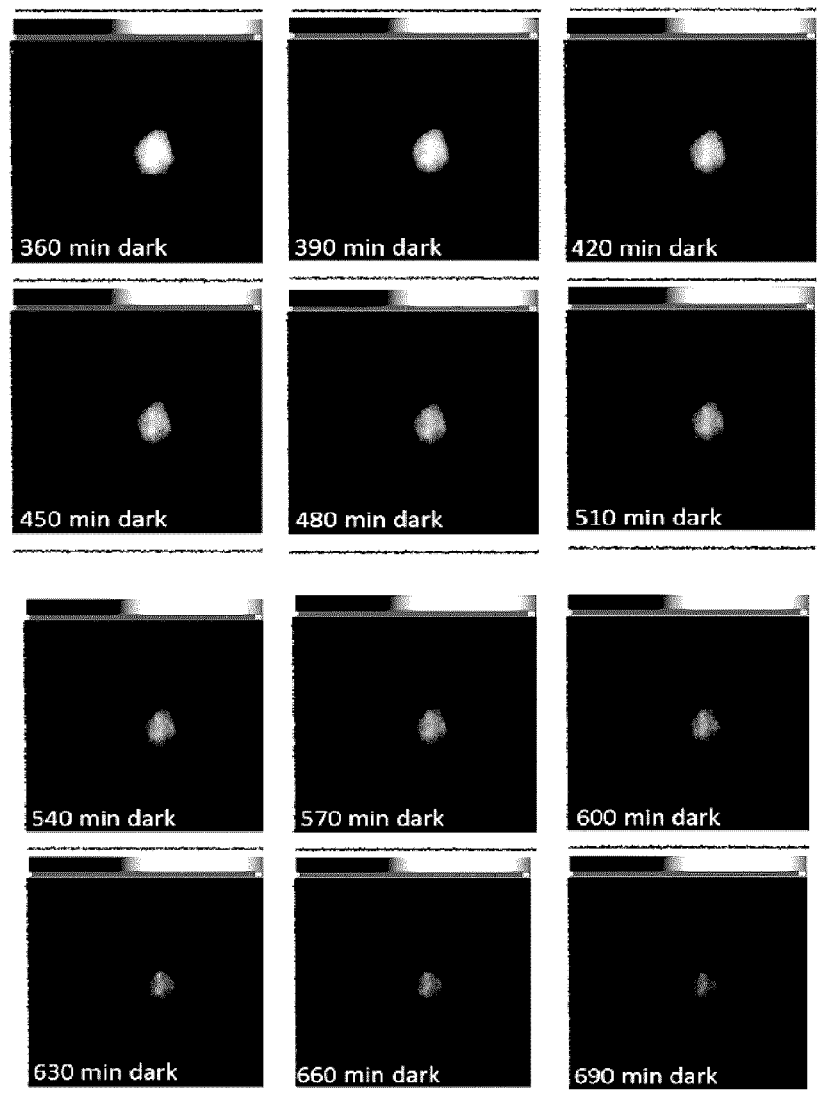
Figure 8:
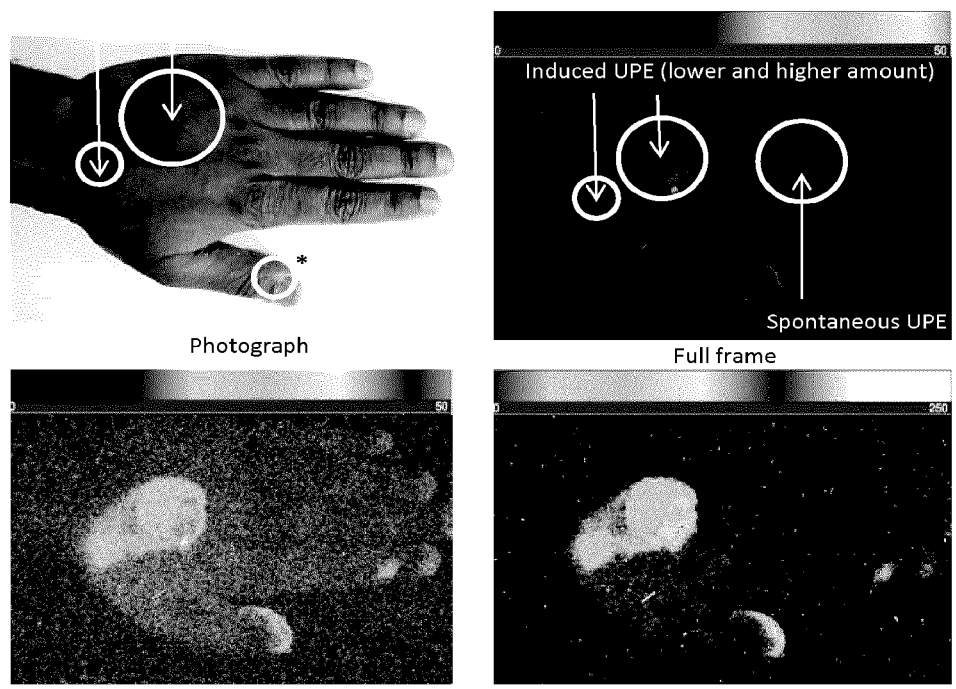
FIG. 8 shows a graph and pictures of the emission of ultra-weak photon from human's skin treated with a biophotonic composition according to one embodiment of the present disclosure comprising light-accepting molecules and illuminated with KLOX™ multi-LED lamp for 5 minutes.

Assay 4: FIGS. 7A-7C show the emission of ultra-weak photon of pig's skin treated with a biophotonic composition comprising 12% UP as well Eosin as light-accepting molecule prior to being illuminated with KLOX™ multi-LED lamp for 5 minutes.

The in situ production and emission of energy by the biological tissue is sustained after the source of fluorescence (i.e., photostimulated light-accepting molecules) has been removed, as demonstrated in the below pictures of the pig's skin subjected to Assay 4 taken at ulterior times. These data indicate that:

Blue light treatment (KLOX™ multi-LED lamp) of the porcine skin sample brings no considerable change in the spatial distribution of ultra-weak photon emission as compared to spontaneous (basal—no biophotonic treatment) ultra-weak photon emission measured in the range of several hours.

Topical application of the blank gel (BPG) only followed by blue light treatment (KLOX™ multi-LED lamp) brings no considerable change as compared to spontaneous basal—no biophotonic treatment) ultra-weak photon emission.

Ultra-weak photon emission was found to be enhanced under the application of the biophotonic compositions. The intensity of ultra-weak photon emission was found to be significantly increased when the skin sample was treated with a biophotonic composition comprising a light-accepting molecule.

The ultra-weak photon emission induced by blue light treatment (KLOX™ multi-LED lamp) in presence of biophotonic compositions was observed in the scale of 0 min-several hours which indicates enhancement of long term metabolic activities. The intensity of ultra-weak photon emission several hours post treatment with the biophotonic composition is variable thereby suggesting different kinetics under variation in the nature of the biophotonic compositions.

These data further demonstrate that the application of a biophotonic composition comprising a light-accepting molecule significantly increases the production and emission of energy by the pig's skin (in-situ energy production and emission). Indeed, FIGS. 7A-7C show that the pig's skin treated with a biophotonic composition comprising Eosin continues emits energy for a longer time and with a stronger intensity than the pig's skin treated with no biophotonic composition or a biophotonic composition without light-accepting molecule. This is particularly observable when comparing FIG. 7C with FIGS. 6B, 5B, 4C and 3B.

Overall, the data indicates that fluorescence emitted from the light-accepting molecules is capable of triggering in situ production and emission of energy by the cells of the biological tissue.

Example 2: Assaying Human Skin with a First Biophotonic Composition

Ultra-weak photon emission (UPE): The CCD camera was located in a dark insulated chamber (with controlled environmental conditions) positioned inside a black painted inner dark room (3 m×1.5 m×2.5 m), whereas the control system was located in the outer dark room as shown in FIG. 2A and FIG. 2B.

The experiment was performed on the human's skin. The two-dimensional photon imaging was performed on a healthy male sited in a relaxed position on a chair. During the course of measurement on the human subject, the use of any kind of cosmetics was avoided. The measurement was performed between 11:00 and 14:00 hrs. The accumulation time was 30 min and duration between application of a biophotonic composition comprising Eosin (+5 min multi-LED lamp) and start of measurement was kept at 30 s. A KLOX™ Multi-LED lamp was used as per the instructions provided by the manufacturer. The intensity at a distance of 5 cm was measured to be ~2800 μmol photons $m^{-2}s^{-1}$. FIGS. 8A-8D show the emission of ultra-weak photon of hand's skin treated with a biophotonic composition comprising Eosin as light-accepting molecule and then illuminated with the multi-LED lamp for 5 minutes. The data presented in FIGS. 8A-8D indicate that the effects observed with pig's skin (Example 1) are also applicable to human tissue.

Example 3: Testing Effects of Variations in Photostimulated Biophotonic Compositions on Energy Emission from Biological Tissue The effects of varying different components of the biophotonic formulations on the energy emission from biological tissue were assessed. To this end, various biophotonic formulations (as indicated in Table 1) were prepared and topically applied onto the pig's skin surface as instructed prior to treatment with light source. Immediately after the light treatment, the biophotonic formulation was wiped completely from the pig's skin surface and washed with double-distilled H₂O at pH 7.0. KLOX Multi-LED™ Lamp (blue/green). The lamp was used as per the instructions provided by the manufacturer. The distance between lamp and sample was kept 5 cm. Illumination time was kept at 7.5 min (blue green lamp). The results are shown in FIGS. 9 to 13.

TABLE 1

Composition of Various Biophotonic Formulations

Figure 9:
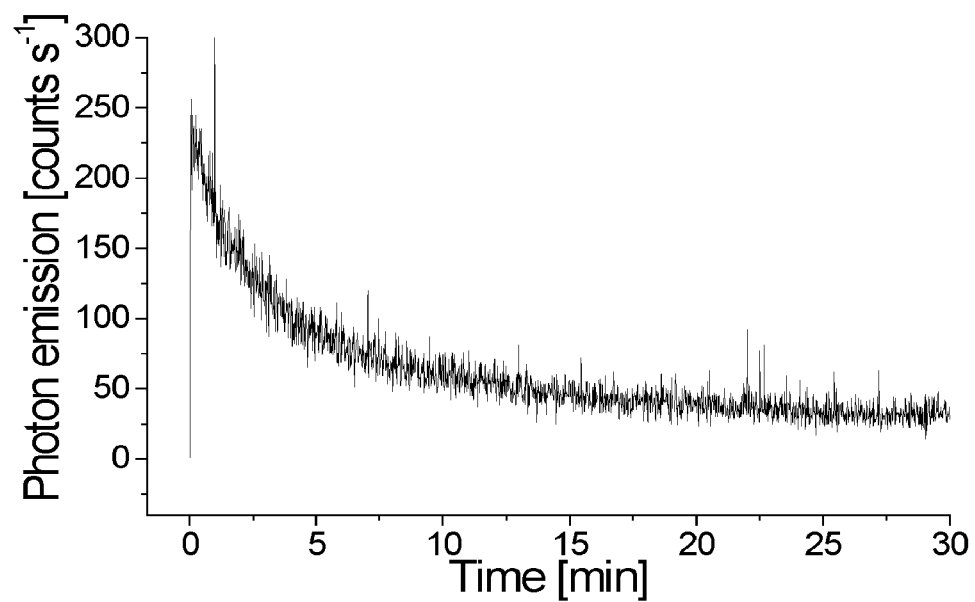
FIG. 9 is a graph showing photon emission over time of a biological tissue photostimulated by a biophotonic composition according to one embodiment of the present technology over time.
Figure 10A:
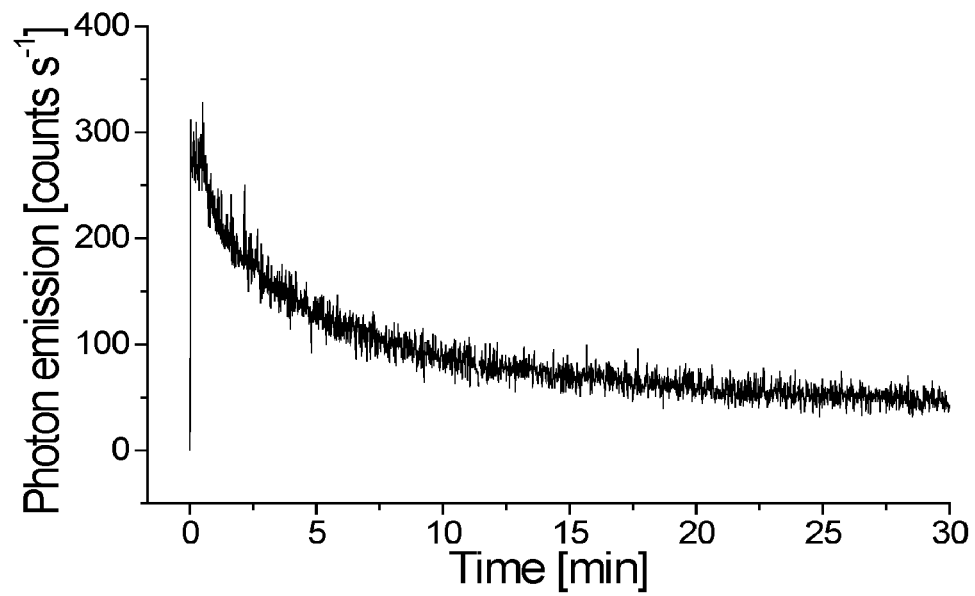
FIGS. 10A-10D are graphs showing photon emission over time of a biological tissue photostimulated by a biophotonic composition according to one embodiment of the present disclosure, wherein the biophotonic compositions comprise varying concentrations of sodium bicarbonate: 1% (FIG. 10A); 3% (FIG. 10B); 5% (FIG. 10C); and 10% (FIG. 10D)
Figure 10B:
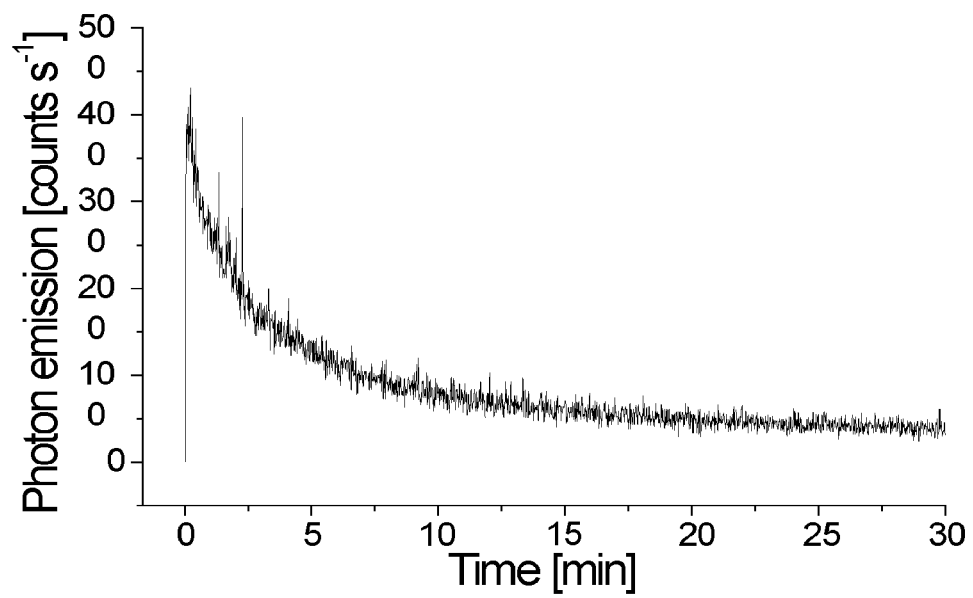
Figure 10C:
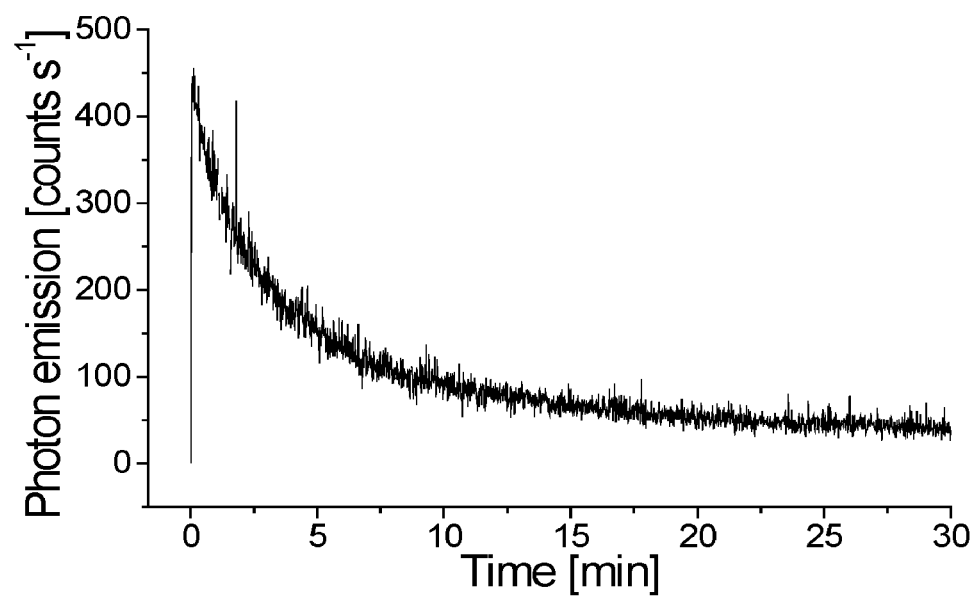
Figure 10D:
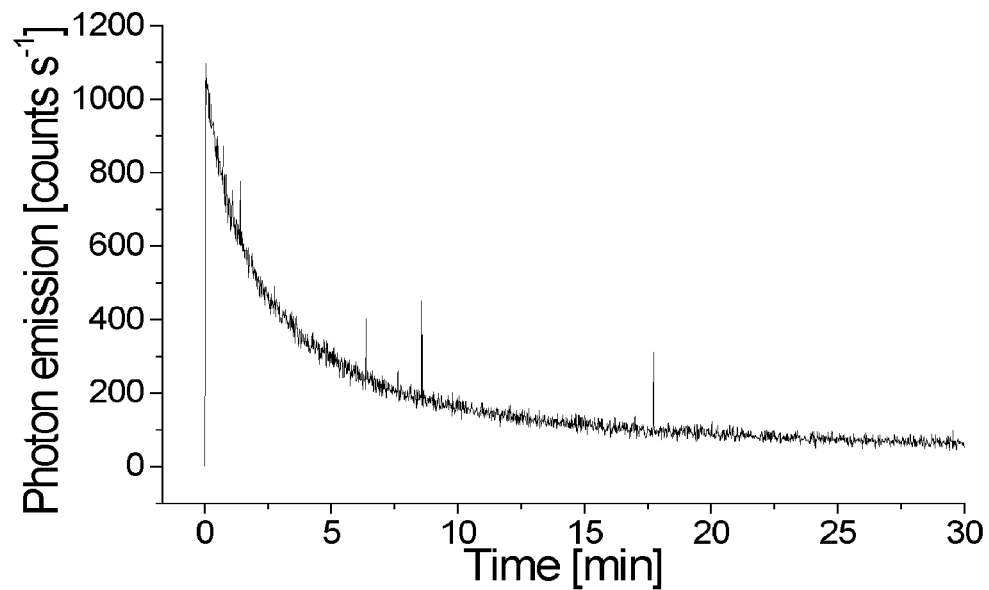
Figure 11A:
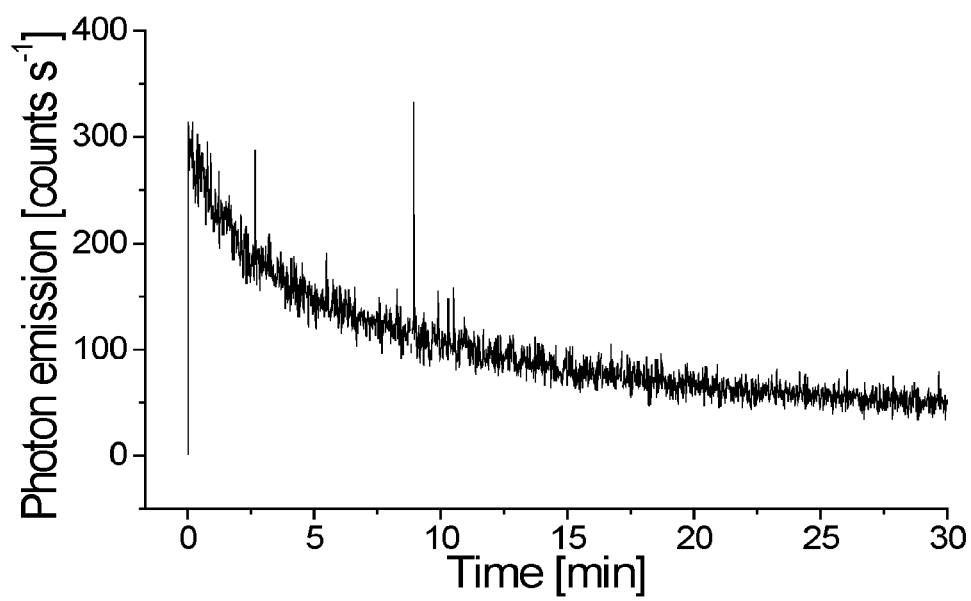
FIGS. 11A-11D are graphs showing photon emission over time of a biological tissue photostimulated by a biophotonic composition according to one embodiment of the present disclosure, wherein the biophotonic compositions comprise varying concentrations of sodium bicarbonate: 1% (FIG. 11A); 3% (FIG. 11B); 5% (FIG. 11C); and 10% (FIG. 11D)
Figure 11B:
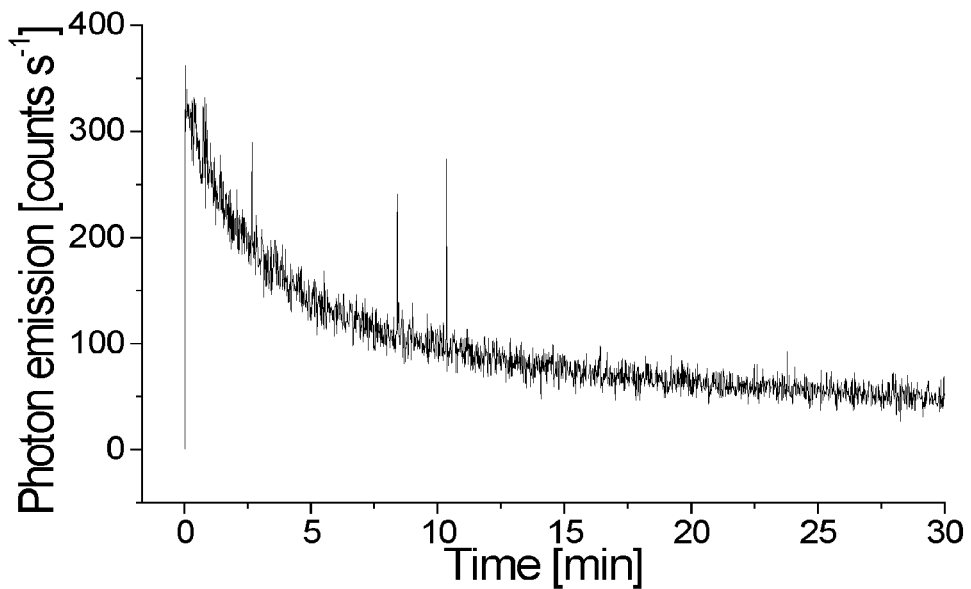
Figure 11C:
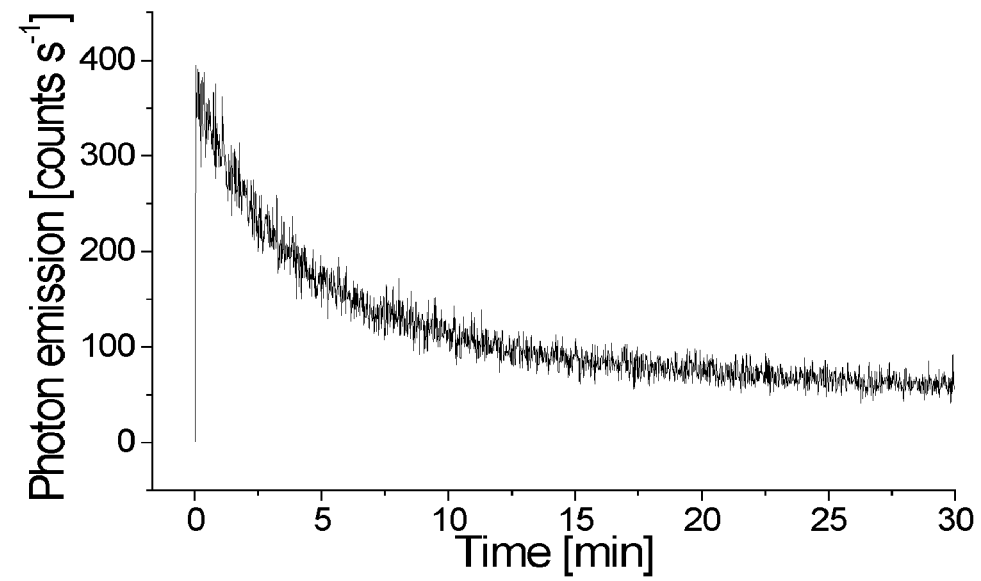
Figure 11D:
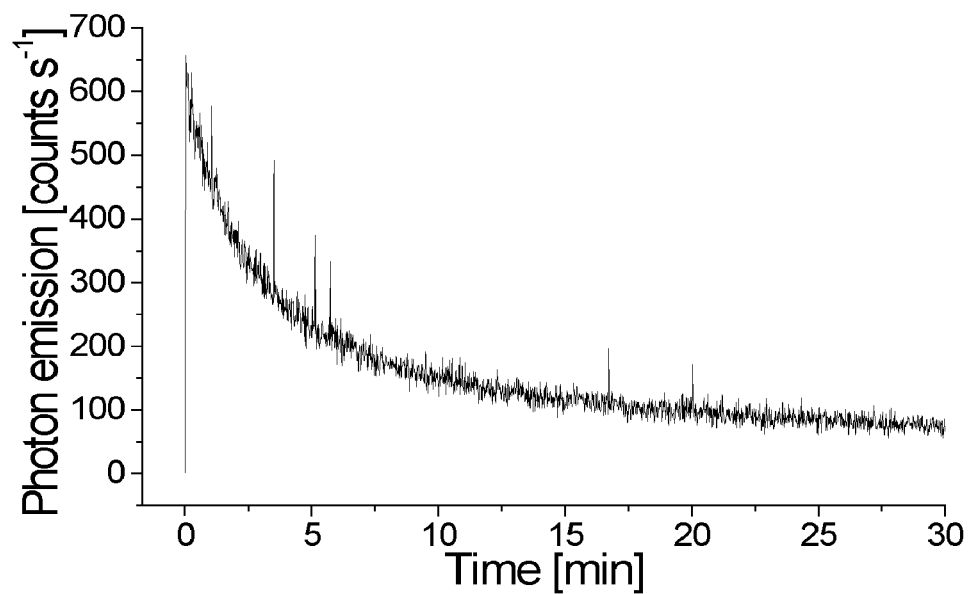
Figure 12A:
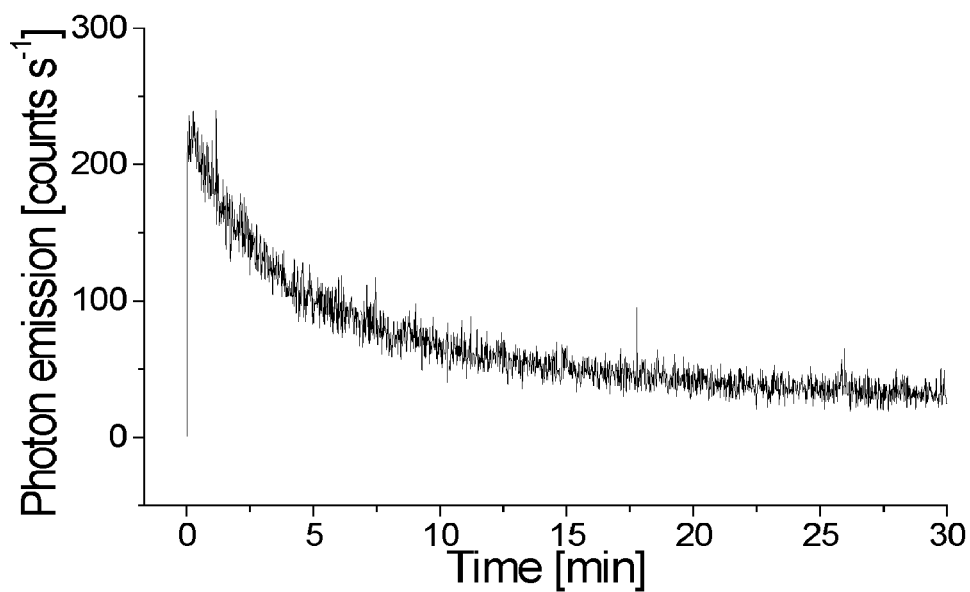
FIGS. 12A-12D are graphs showing photon emission over time of a biological tissue photostimulated by a biophotonic composition according to one embodiment of the present disclosure, wherein the biophotonic compositions comprise varying concentrations of sodium bicarbonate: 1% (FIG. 12A); 3% (FIG. 12B); 5% (FIG. 12C); and 10% (FIG. 12D)
Figure 12B:
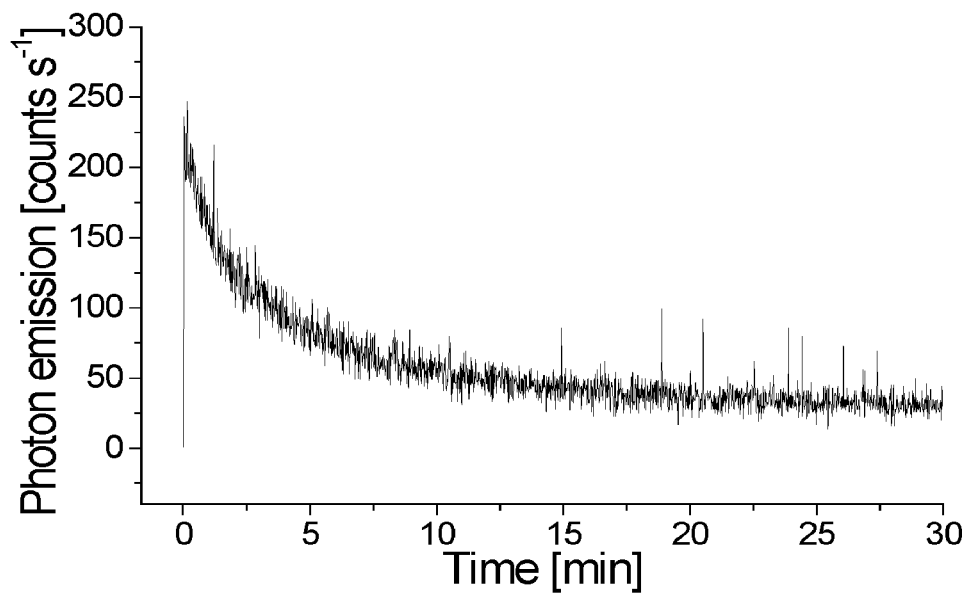
Figure 12C:
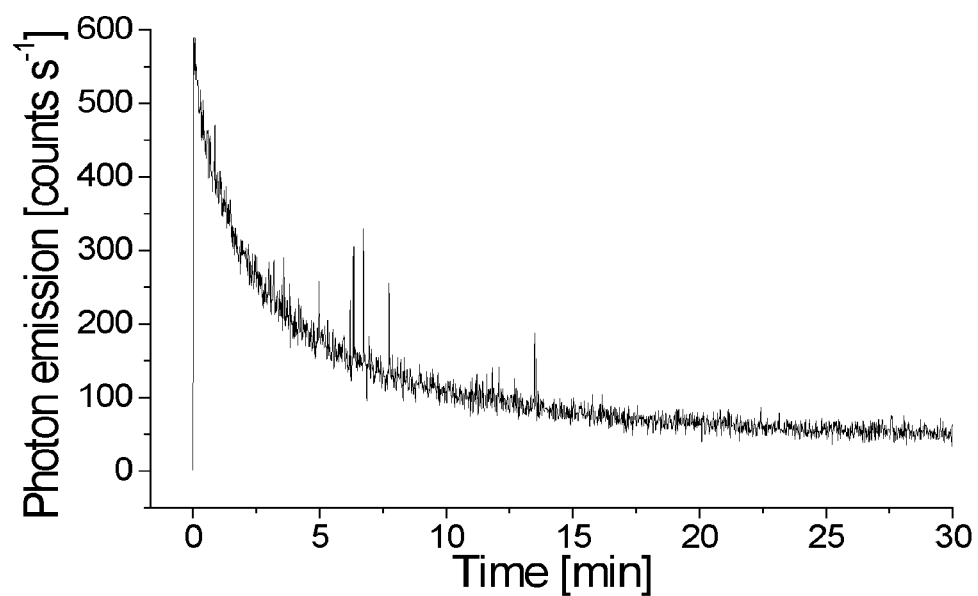
Figure 12D:
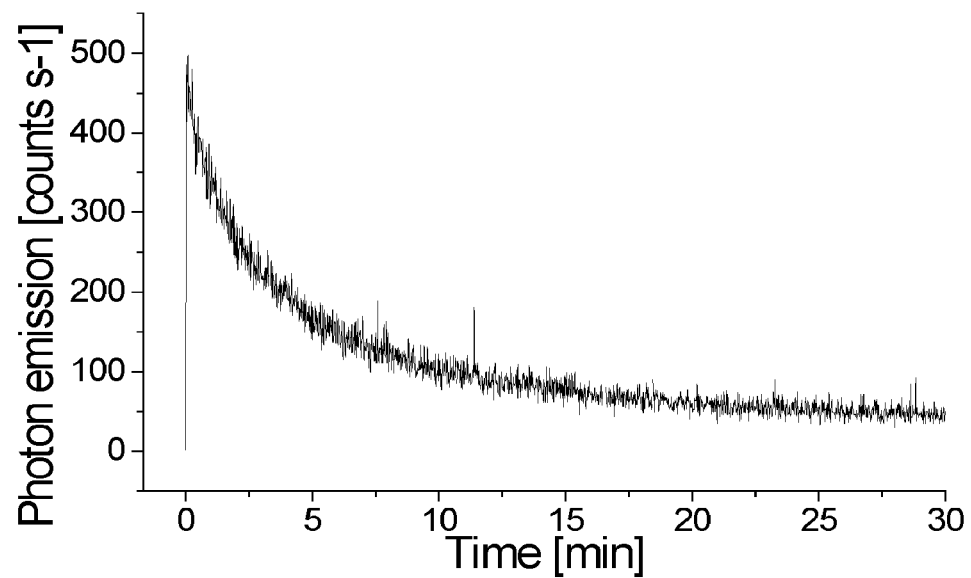
Figure 13A:
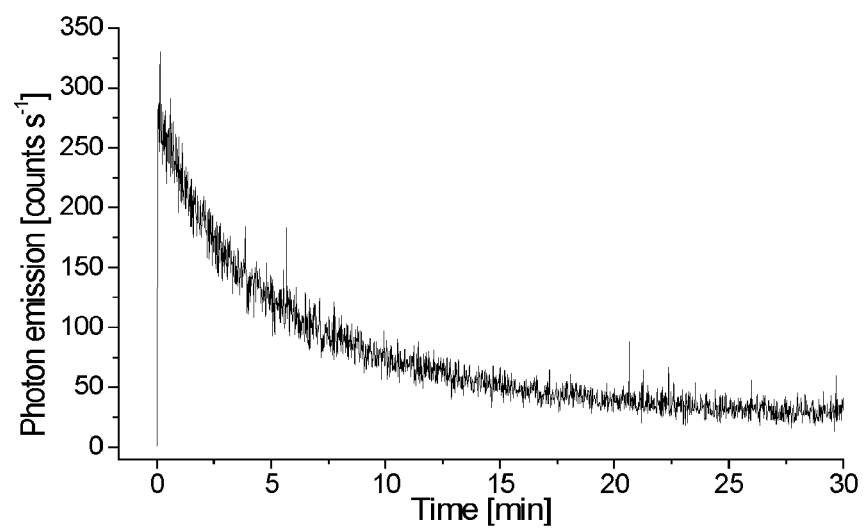
FIGS. 13A-13D are graphs showing photon emission over time of a biological tissue photostimulated by a biophotonic composition according to one embodiment of the present disclosure, wherein the biophotonic compositions comprise varying concentrations of sodium bicarbonate: 1% (FIG. 13A); 3% (FIG. 13B); 5% (FIG. 13C); and 10% (FIG. 13D)
Figure 13B:
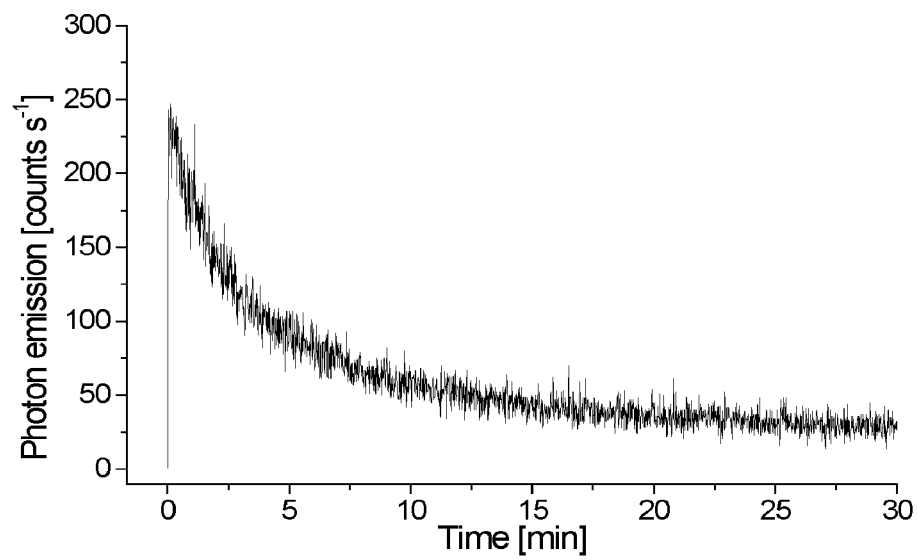
Figure 13C:
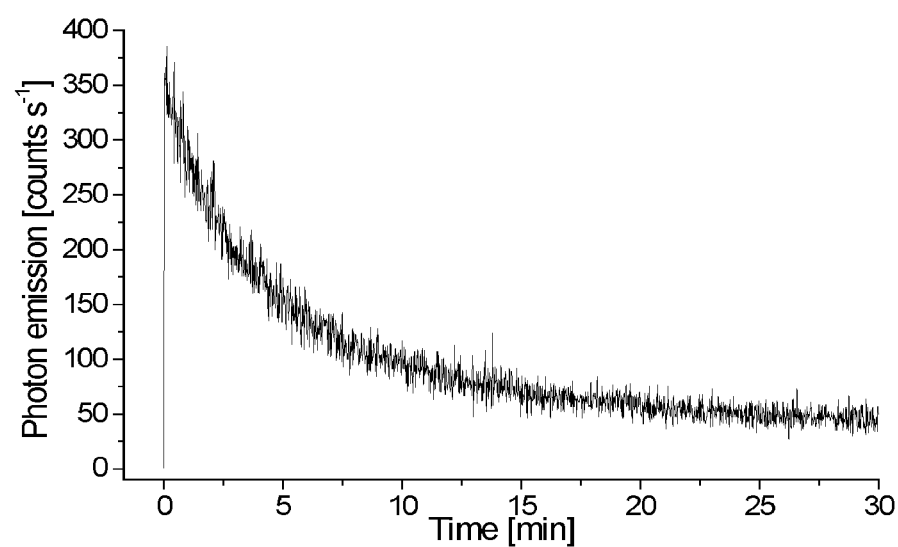
Figure 13D:
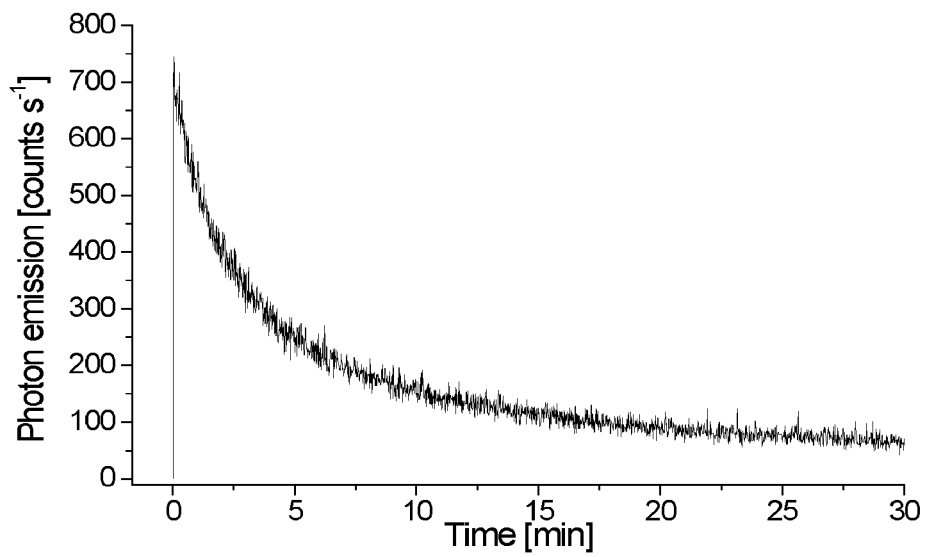

| Biophotonic Formulation | NaHCO₃ (in wt % of the total wt of the biophotonic formulation) | | | |
|---|---|---|---|---|
| A | 0 | | | |
| (Eosin Y, no Urea peroxide (UP)) | FIG. 9 | | | |
| | 1 | 3 | 5 | 10 |
| B (Eosin Y, no UP) | FIG. 10A | FIG. 10B | FIG. 10C | FIG. 10D |
| C (Eosin Y + Rose Bengal, no UP) | FIG. 11A | FIG. 11B | FIG. 11C | FIG. 11D |
| D (Rose Bengal + Rieshi, no UP) | FIG. 12A | FIG. 12B | FIG. 12C | FIG. 12D |
| E (Eosin Y + Rieshi, no UP) | FIG. 13A | FIG. 13B | FIG. 13C | FIG. 13D |

The results presented in FIGS. 10A-10D demonstrate that photon emission increases in presence of an increasing concentration of NaHCO₃ in the biophotonic formulation. The same phenomenon was observed for biophotonic formulations B (FIGS. 11A-11D), biophotonic formulation C (FIGS. 12A-12D) and for biophotonic formulation D (FIGS. 13A-13D).

The data also demonstrates that the nature of the light-absorbing molecule present in the biophotonic formulation has an effect on photon emission by the photostimulated skin. For every concentration of NaHCO₃ tested, a biophotonic composition comprising Eosin Y (FIGS. 10A-10D) generated a higher photon emission than with a combination of Eosin Y and Rose Bengal (FIGS. 11A-11D), Rose Bengal and Rieshi (FIGS. 12A-12D) or Eosin Y and Rieshi (FIGS. 13A-13D).

Determination of the PE Index for Biophotonic Composition B comprising different concentrations of sodium bicarbonate:

FIG. 10A=Photon emission at time 0=300 counts× 50%=150 counts; PE=about 3 minutes (time it takes biophotonic composition B to emit about 150 counts);

FIG. 10B=Photon emission at time 0=400 counts× 50%=200 counts; PE=about 2.5 minutes (time it takes biophotonic composition B to emit about 200 counts);

FIG. 10C=Photon emission at time 0=450 counts× 50%=225 counts; PE=about 2.5 minutes (time it takes biophotonic composition B to emit about 225 counts);

FIG. 10D=Photon emission at time 0=1050 counts× 50%=525 counts; PE=about 2.5 minutes (time it takes biophotonic composition B to emit about 525 counts).

Determination of the PE Index for Biophotonic Composition C comprising different concentrations of sodium bicarbonate:

FIG. 11A=Photon emission at time 0=300 counts× 50%=150 counts; PE=about 4 minutes (time it takes biophotonic composition B to emit about 150 counts);

FIG. 11B=Photon emission at time 0=325 counts× 50%=163 counts; PE=about 3 minutes (time it takes biophotonic composition B to emit about 163 counts);

FIG. 11C=Photon emission at time 0=375 counts× 50%=188 counts; PE=about 4 minutes (time it takes biophotonic composition B to emit about 188 counts);

FIG. 11D=Photon emission at time 0=650 counts× 50%=325 counts; PE=about 2.5 minutes (time it takes biophotonic composition B to emit about 325 counts).

Determination of the PE Index for Biophotonic Composition D comprising different concentrations of sodium bicarbonate:

FIG. 12A=Photon emission at time 0=250 counts× 50%=125 counts; PE=about 3 minutes (time it takes biophotonic composition B to emit about 125 counts);

FIG. 12B=Photon emission at time 0=225 counts× 50%=113 counts; PE=about 4 minutes (time it takes biophotonic composition B to emit about 113 counts);

FIG. 12C=Photon emission at time 0=550 counts× 50%=275 counts; PE=about 2.5 minutes (time it takes biophotonic composition B to emit about 275 counts);

FIG. 12D=Photon emission at time 0=650 counts× 50%=325 counts; PE=about 2.5 minutes (time it takes biophotonic composition B to emit about 325 counts).

Determination of the PE Index for Biophotonic Composition E comprising different concentrations of sodium bicarbonate:

FIG. 13A=Photon emission at time 0=350 counts× 50%=175 counts; PE=about 2.5 minutes (time it takes biophotonic composition B to emit about 175 counts);

FIG. 13B=Photon emission at time 0=250 counts× 50%=125 counts; PE=about 2.5 minutes (time it takes biophotonic composition B to emit about 125 counts);

FIG. 13C=Photon emission at time 0=350 counts× 50%=125 counts; PE=about 5 minutes (time it takes biophotonic composition B to emit about 125 counts);

FIG. 13D=Photon emission at time 0=700 counts× 50%=350 counts; PE=about 2.5 minutes (time it takes biophotonic composition B to emit about 350 counts).

Example 4: Testing Effects of Variations in Photostimulated Biophotonic Compositions on Energy Emission from Biological Tissue The effects of varying different components of the biophotonic formulations on the energy emission from biological tissue were assessed. To this end, various biophotonic formulations (as indicated in Table 2) were prepared and topically applied onto the pig's skin surface as instructed prior to treatment with light source. Immediately after the light treatment, the biophotonic formulation was wiped completely from the pig's skin surface and washed with double-distilled H₂O at pH 7.0. KLOX Multi-LED™ Lamp (blue/green). The lamp was used as per the instructions provided by the manufacturer. The distance between lamp and sample was kept 5 cm. Illumination time was kept at 7.5 min (blue green lamp). The results are shown in FIGS. 14 to 17.

TABLE 2

Composition of Various Biophotonic Formulations

Figure 14A:
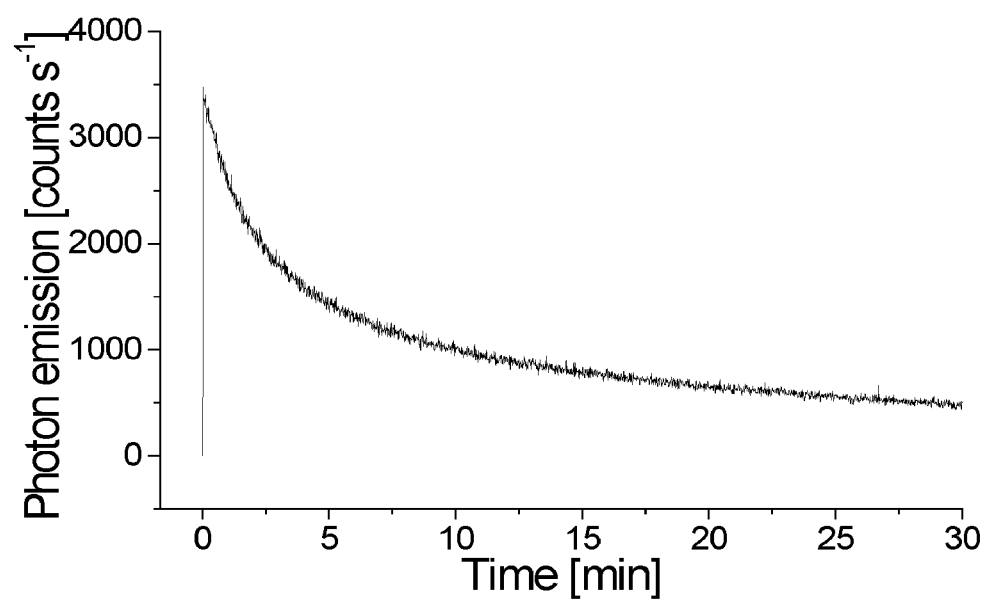
FIGS. 14A-14C are graphs showing photon emission over time of a biological tissue photostimulated by a biophotonic composition according to one embodiment of the present disclosure, wherein the biophotonic compositions comprise varying concentrations of urea peroxide (UP): 3% (FIG. 14A); 6% (FIG. 14B); and 12% (FIG. 14C)
Figure 14B:
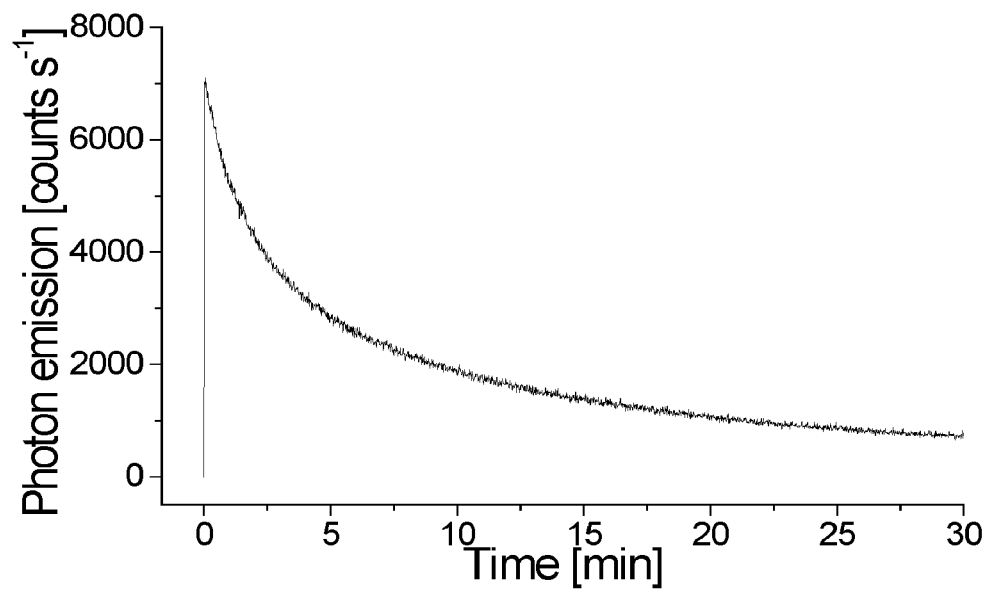
Figure 14C:
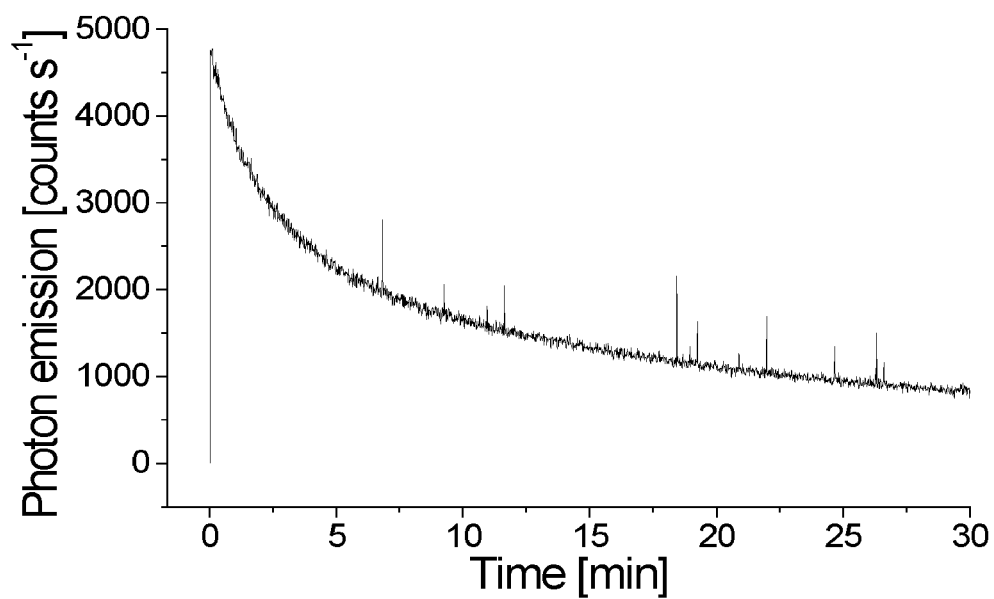
Figure 15A:
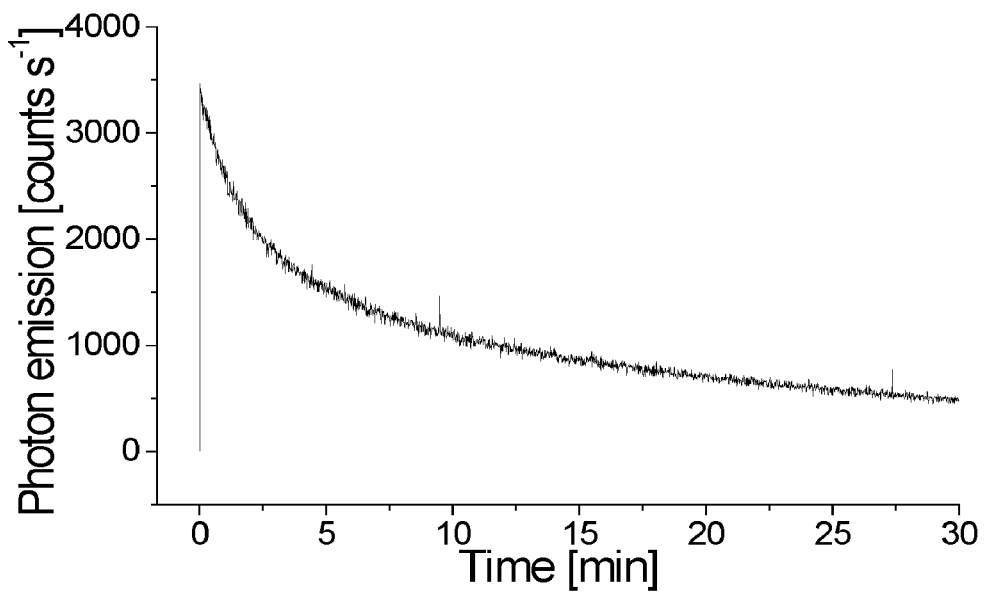
FIGS. 15A-15C are graphs showing photon emission over time of a biological tissue photostimulated by a biophotonic composition according to one embodiment of the present disclosure, wherein the biophotonic compositions comprise varying concentrations of urea peroxide (UP): 3% (FIG. 15A); 6% (FIG. 15B); and 12% (FIG. 15C)
Figure 15B:
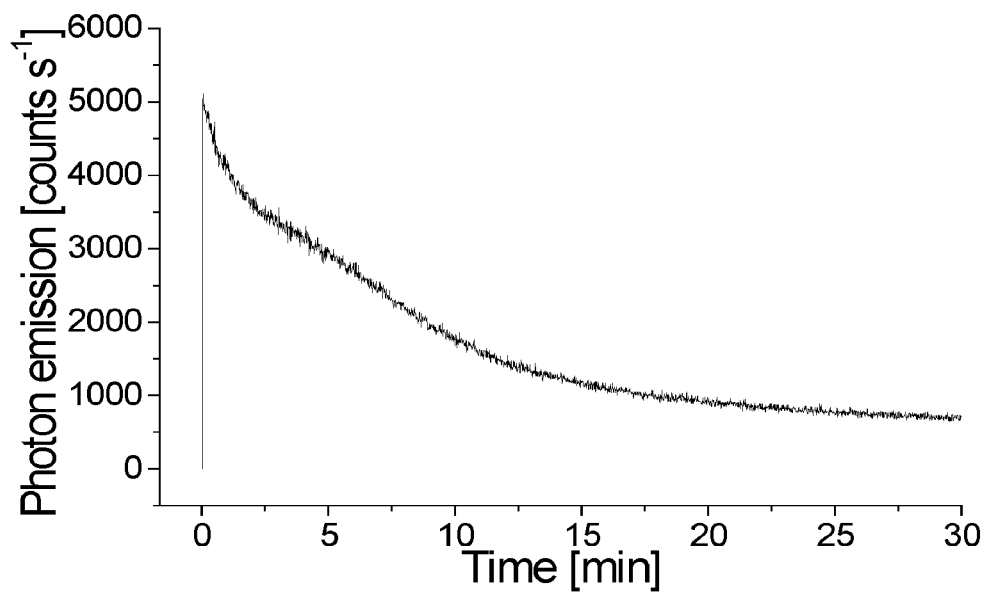
Figure 15C:
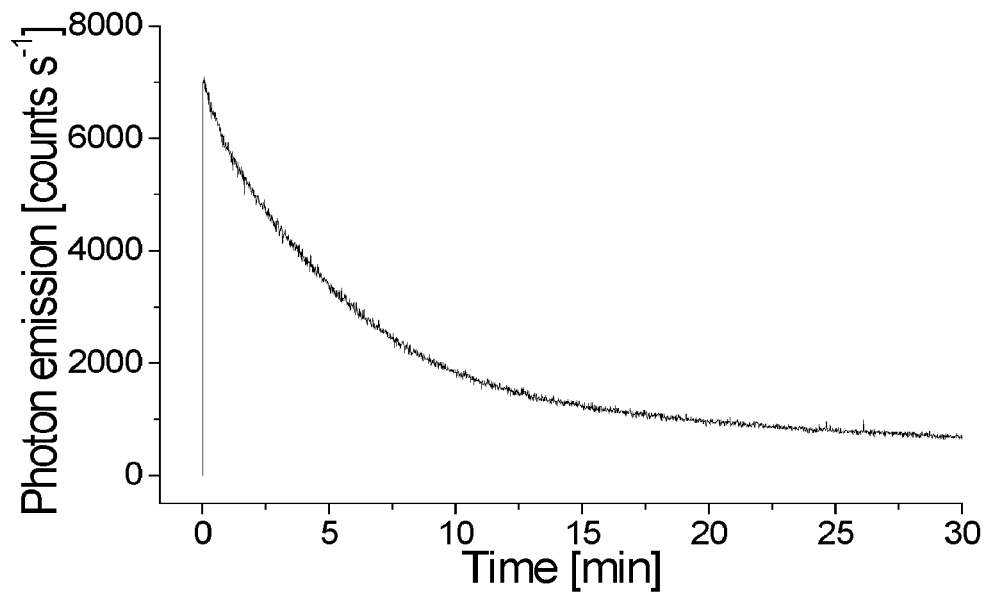
Figure 16A:
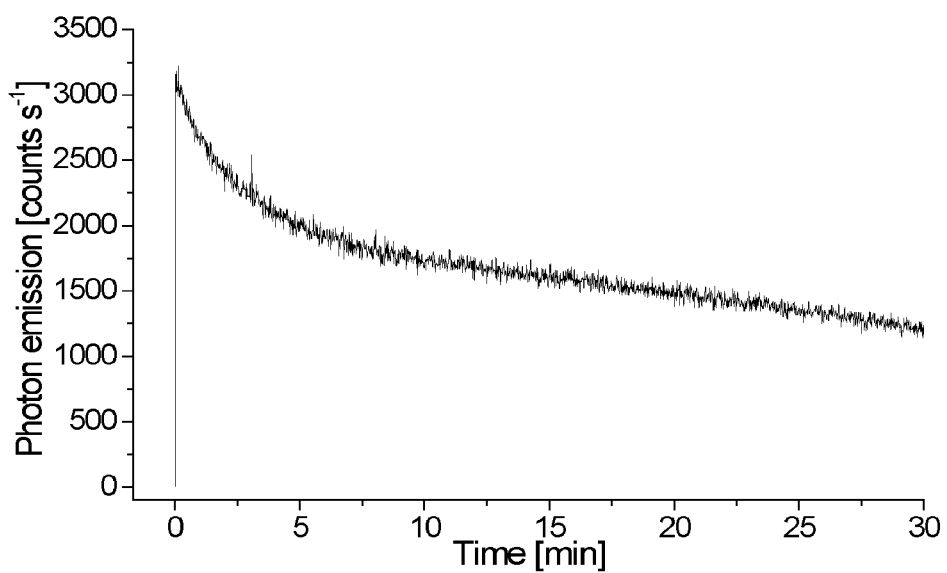
FIGS. 16A-16C are graphs showing showing photon emission over time of a biological tissue photostimulated by a biophotonic composition according to one embodiment of the present disclosure, wherein the biophotonic compositions comprise varying concentrations of urea peroxide (UP): 3% (FIG. 16A); 6% (FIG. 16B); and 12% (FIG. 16C)
Figure 16B:
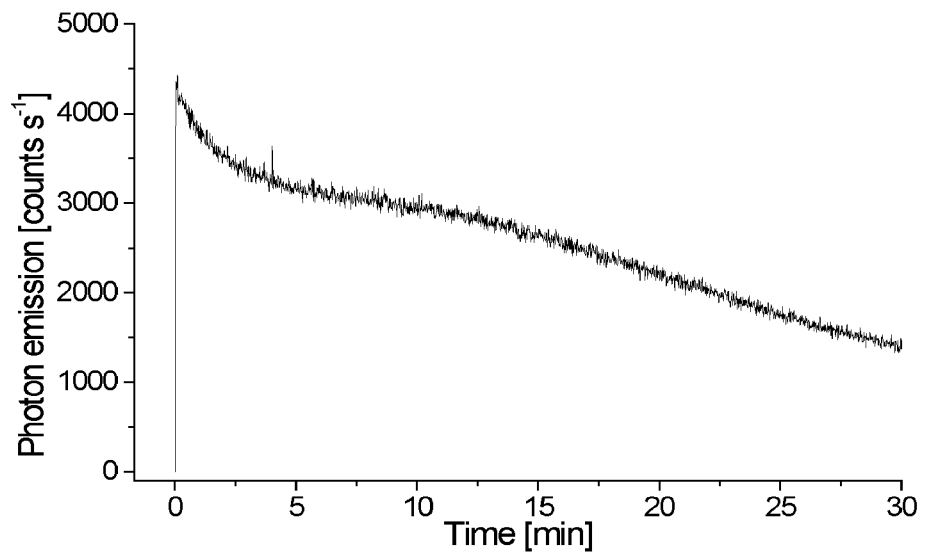
Figure 16C:
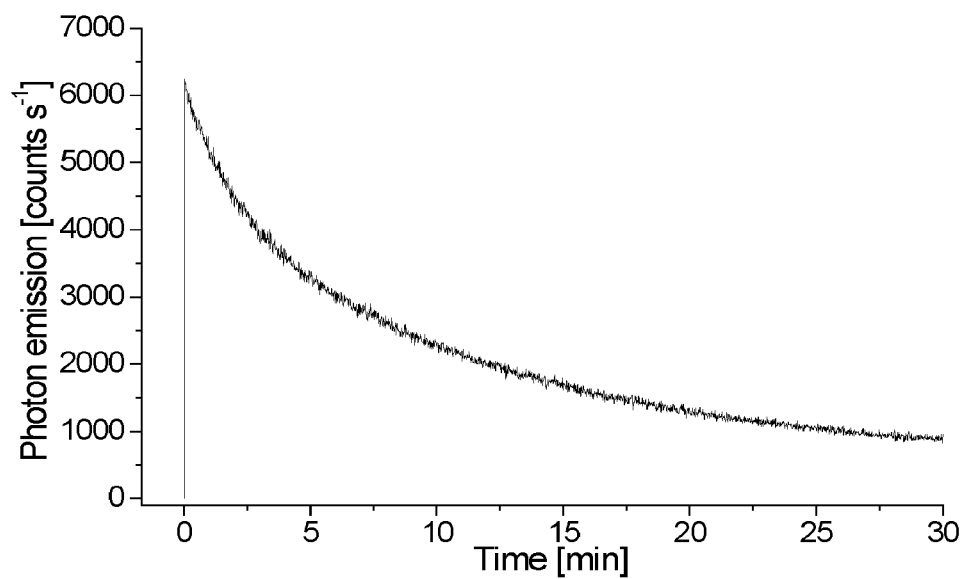
Figure 17A:
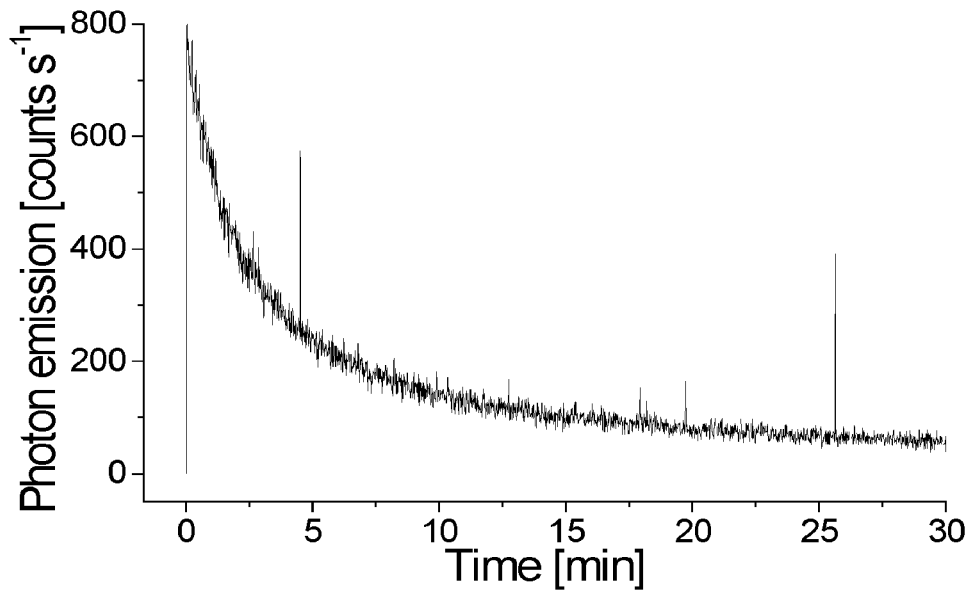
FIGS. 17A-17C are graphs showing photon emission over time of a biological tissue photostimulated by a biophotonic composition according to one embodiment of the present disclosure, wherein the biophotonic compositions comprise varying concentrations of urea peroxide (UP): 3% (FIG. 17A); 6% (FIG. 17B); and 12% (FIG. 17C).
Figure 17B:
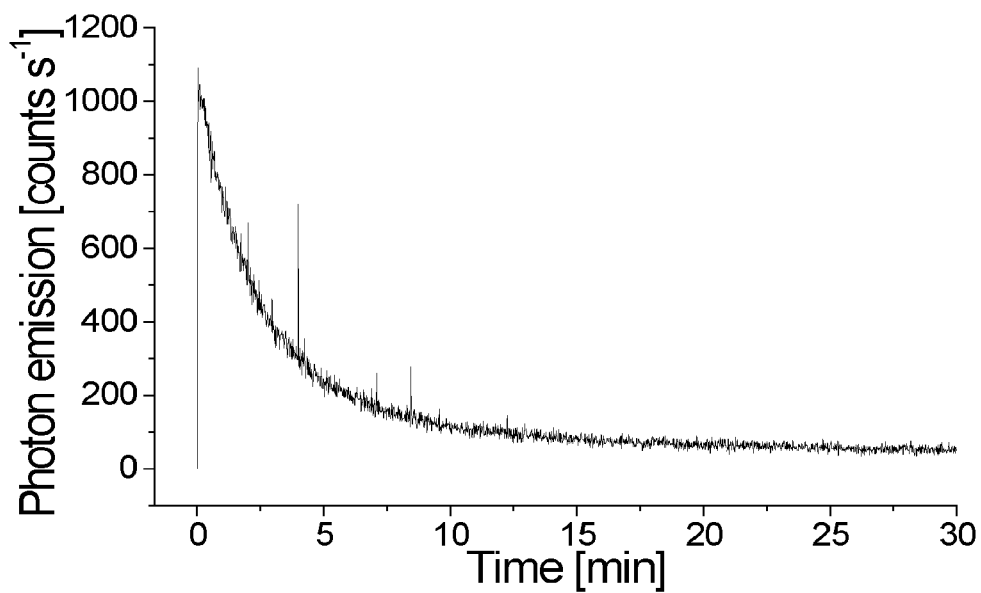
Figure 17C:
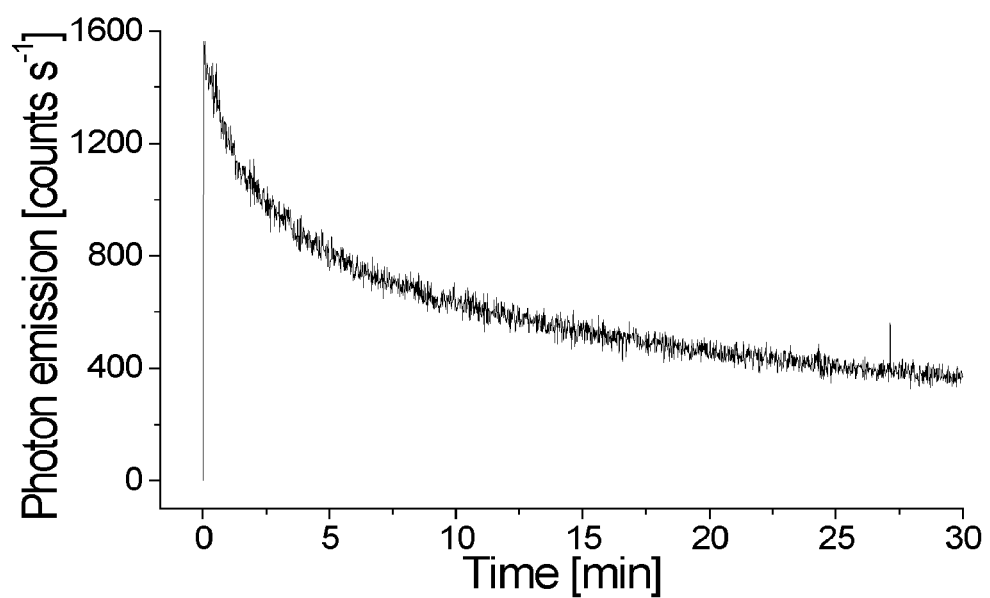

| Biophotonic Formulation | Urea Peroxide (UP) (in wt % of the total wt of the biophotonic formulation) | | |
| --- | --- | --- | --- |
| | 3 | 6 | 12 |
| F (Eosin Y) | FIG. 14A | FIG. 14B | FIG. 14C |
| G (Eosin Y + Rose Bengal) | FIG. 15A | FIG. 15B | FIG. 15C |
| H (Eosin Y + Rieshi) | FIG. 16A | FIG. 16B | FIG. 16C |
| I (Rose Bengal + rieshi) | FIG. 17A | FIG. 17B | FIG. 17C |

The results presented in FIGS. 15A-15C, 16A-16C and 17A-17C demonstrate that photon emission increases in presence of an increasing concentration of urea peroxide in the biophotonic formulation. However, in the case of biophotonic formulation comprising Eosin Y (FIGS. 14A-14D), a concentration of 12% UP (FIG. 14C) gave rise to a photon emission lower than with 6% UP (FIG. 14B indicating the level of urea peroxide at which the ability of Eosin Y to act as a light-absorbing molecule are affected.

Determination of the PE Index for Biophotonic Composition F comprising different concentrations of urea peroxide:

FIG. 14A=Photon emission at time 0=3500 counts× 50%=1750 counts; PE=about 4 minutes (time it takes biophotonic composition B to emit about 1750 counts);

FIG. 14B=Photon emission at time 0=7000 counts× 50%=3500 counts; PE=about 4 minutes (time it takes biophotonic composition B to emit about 3500 counts);

FIG. 14C=Photon emission at time 0=4500 counts× 50%=2250 counts; PE=about 5 minutes (time it takes biophotonic composition B to emit about 2250 counts).

Determination of the PE Index for Biophotonic Composition G comprising different concentrations of urea peroxide:

FIG. 15A=Photon emission at time 0=3500 counts× 50%=1750 counts; PE=about 3 minutes (time it takes biophotonic composition B to emit about 1750 counts);

FIG. 15B=Photon emission at time 0=5000 counts× 50%=2500 counts; PE=about 7 minutes (time it takes biophotonic composition B to emit about 2500 counts);

FIG. 15C=Photon emission at time 0=7000 counts× 50%=3500 counts; PE=about 5 minutes (time it takes biophotonic composition B to emit about 3500 counts).

Determination of the PE Index for Biophotonic Composition H comprising different concentrations of urea peroxide:

FIG. 16A=Photon emission at time 0=3250 counts× 50%=1625 counts; PE=about 10 minutes (time it takes biophotonic composition B to emit about 1625 counts);

FIG. 16B=Photon emission at time 0=4250 counts× 50%=2125 counts; PE=about 17.5 minutes (time it takes biophotonic composition B to emit about 2125 counts);

FIG. 16C=Photon emission at time 0=6000 counts× 50%=3000 counts; PE=about 6 minutes (time it takes biophotonic composition B to emit about 3000 counts).

Determination of the PE Index for Biophotonic Composition I comprising different concentrations of urea peroxide:

FIG. 17A=Photon emission at time 0=800 counts× 50%=400 counts; PE=about 2.5 minutes (time it takes biophotonic composition B to emit about 400 counts);

FIG. 17B=Photon emission at time 0=1050 counts× 50%=525 counts; PE=about 2.5 minutes (time it takes biophotonic composition B to emit about 525 counts);

FIG. 17C=Photon emission at time 0=1500 counts× 50%=750 counts; PE=about 5 minutes (time it takes biophotonic composition B to emit about 750 counts).

It should be appreciated that the disclosure is not limited to the particular embodiments described and illustrated herein but includes all modifications and variations falling within the scope of the subject matters as defined in the appended claims.

Incorporation by Reference

All references cited in this specification, and their references, are incorporated by reference herein in their entirety where appropriate for teachings of additional or alternative details, features, and/or technical background.

Equivalents

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following embodiments.

The invention claimed is:

1. A method for modulating in situ production of energy by a biological tissue, the method comprising stimulating the biological tissue by exposing the biological tissue to a therapeutically effective amount of a photostimulated biophotonic composition for a time sufficient to initiate the production of energy by the biological tissue, wherein the energy is ultra-weak photon emission.

2. The method as defined in claim 1, wherein the biophotonic composition comprises one or more light-accepting molecules.

3. The method as defined in claim 2, wherein the one or more light-accepting molecules are xanthene dyes.

4. The method as defined in claim 2, wherein the one or more light-accepting molecules include Eosin.

5. The method as defined in claim 2, wherein the one or more light-accepting molecules include Rose Bengal.

6. The method as defined in claim 2, wherein the biophotonic composition further comprises Reishi.

7. The method as defined in claim 1, wherein the biophotonic composition further comprises a carbonate salt, or a bicarbonate salt, or both.

8. The method as defined in claim 1, wherein the biophotonic composition further comprises a carbonate salt.

9. The method as defined in claim 1, wherein the biophotonic composition further comprises a bicarbonate salt.

10. The method as defined in claim 8, wherein the carbonate salt is selected from: barium carbonate, beryllium carbonate, caesium carbonate, calcium carbonate, cobalt (II) carbonate, copper (II) carbonate, lithium carbonate, magnesium carbonate, nickel (II) carbonate, potassium carbonate, sodium carbonate, and zinc carbonate.

11. The method as defined in claim 9, wherein the bicarbonate salt is selected from: ammonium bicarbonate, caesium bicarbonate, potassium bicarbonate, sodium bicarbonate, choline bicarbonate, aminoguanidine bicarbonate, and tetraethylammonium bicarbonate.

12. The method as defined in claim 1, wherein the biological tissue is a skin tissue.

13. The method as defined in claim 1, wherein the biological tissue is a population of cells.

14. The method as defined in claim 1, wherein the photostimulated biophotonic composition emits fluorescence.

15. The method as defined in claim 14, wherein the fluorescence photostimulates the biological tissue.

16. The method as defined in claim 15, wherein the photostimulated biological tissue emits photons.

17. The method as defined in claim 1, wherein the biophotonic composition has a photon emission index of at least 30 seconds.

18. The method as defined in claim 1, wherein the biophotonic composition has a photon emission index of at least 2 minutes.

19. The method as defined in claim 1, wherein the biophotonic composition has a photon emission index of at least 30 seconds, or at least 1 minute, or least 2 minutes, or at least 3 minutes, or at least 4 minutes, or at least 5 minutes, or at least 6 minutes, or at least 7 minutes, or at least 8 minutes, or at least 9 minutes, or at least 10 minutes.

* * * * *